United States Patent
Schmidt et al.

(10) Patent No.: US 9,862,994 B2
(45) Date of Patent: Jan. 9, 2018

(54) SELECTIVE NUCLEIC ACID AMPLIFICATION FROM NUCLEIC ACID POOLS

(71) Applicant: Dana-Farber Cancer Institute, Inc., Boston, MA (US)

(72) Inventors: Thorsten Lars Schmidt, Jamaica Plain, MA (US); Mark Theilmann, Summerland (CA); William M. Shih, Cambridge, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 208 days.

(21) Appl. No.: 14/376,241

(22) PCT Filed: Feb. 8, 2013

(86) PCT No.: PCT/US2013/025246
§ 371 (c)(1),
(2) Date: Aug. 1, 2014

(87) PCT Pub. No.: WO2013/119888
PCT Pub. Date: Aug. 15, 2013

(65) Prior Publication Data
US 2015/0024972 A1 Jan. 22, 2015

Related U.S. Application Data

(60) Provisional application No. 61/596,821, filed on Feb. 9, 2012.

(51) Int. Cl.
*C12Q 1/68* (2006.01)

(52) U.S. Cl.
CPC ..... *C12Q 1/6844* (2013.01); *C12Q 2563/155* (2013.01)

(58) Field of Classification Search
None
See application file for complete search history.

(56) References Cited

U.S. PATENT DOCUMENTS

| 5,436,149 A | 7/1995 | Barnes |
| 2007/0117109 A1 | 5/2007 | Rothemund |

(Continued)

FOREIGN PATENT DOCUMENTS

| DK | WO 2006108423 A2 * 10/2006 ............. C12N 15/10 |
| WO | WO 01/57256 A2  8/2001 |

(Continued)

OTHER PUBLICATIONS

Ando et al., Isolation and characterization of enzymes with nicking action from phage T4-infected *Escherichia coli*. J Biochem. Jul. 1969;66(1):1-10.

(Continued)

*Primary Examiner* — Karen S Weiler
(74) *Attorney, Agent, or Firm* — Wolf, Greenfield & Sacks, P.C.

(57) ABSTRACT

Provided herein are nucleic acids and methods for selectively amplifying in parallel tens of thousands of high quality oligonucleotides without common sequences. The resultant oligonucleotides can be used for a variety of purposes and applications including but not limited to DNA nano structure synthesis.

16 Claims, 12 Drawing Sheets

(56) References Cited

U.S. PATENT DOCUMENTS

| | | |
|---|---|---|
| 2012/0035065 A1 | 2/2012 | Smolke et al. |
| 2013/0072390 A1* | 3/2013 | Wang .................... C12P 19/28 506/9 |
| 2016/0153036 A1 | 6/2016 | Chen et al. |

FOREIGN PATENT DOCUMENTS

| | | | |
|---|---|---|---|
| WO | WO 02/22882 A2 | 3/2002 | |
| WO | WO 03/095664 A2 | 11/2003 | |
| WO | WO 2004/044549 A2 | 5/2004 | |
| WO | WO 2006/105285 A1 | 10/2006 | |
| WO | WO 2006/108423 A2 | 10/2006 | |
| WO | WO 2007/106534 A2 | 9/2007 | |
| WO | WO 2008/104794 A2 | 9/2008 | |
| WO | WO2010120853 A2 * | 10/2010 | .............. C12Q 1/68 |
| WO | WO 2012/058488 A1 | 5/2012 | |
| WO | WO 2015/010020 A1 | 1/2016 | |

OTHER PUBLICATIONS

Baner et al., Signal amplification of padlock probes by rolling circle replication. Nucleic Acids Res. 1998 Nov 15;26(22):5073-8.

Bellot et al., Recovery of intact DNA nanostructures after agarose gel-based separation. Nat Methods. Mar. 2011;8(3):192-4. doi: 10.1038/nmeth0311-192.

Cha et al., Mismatch amplification mutation assay (MAMA): application to the c-H-ras gene. PCR Methods Appl. Aug. 1992;2(1):14-20.

Dahl et al., Circle-to-circle amplification for precise and sensitive DNA analysis. Proc Natl Acad Sci U S A. Mar. 30, 2004;101(13):4548-53. Epub Mar. 15, 2004.

Dietz et al., Folding DNA into twisted and curved nanoscale shapes. Science. Aug. 7, 2009;325(5941):725-30. doi: 10.1126/science. 1174251.

Dirks et al., Thermodynamic Analysis of Interacting Nucleic Acid Strands. SIAM Rev. 2007;49(1):65-88.

Dirks et al., Triggered amplification by hybridization chain reaction. PNAS. 2004;101: 15275-78.

Dobosy et al., RNase H-dependent PCR (rhPCR): improved specificity and single nucleotide polymorphism detection using blocked cleavable primers. BMC Biotechnol. Aug. 10, 2011;11:80. doi:10.1186/1472-6750-11-80.

Dominguez et al. Wild-type blocking polymerase chain reaction for detection of single nucleotide minority mutations from clinical specimens. Oncogene. Oct. 13, 2005;24(45):6830-4.

Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.

Douglas et al., Self-assembly of DNA into nanoscale three-dimensional shapes. Nature. May 21, 2009;459(7245):414-8. Available in PMC Nov. 21, 2009.

Ducani et al., Rolling circle replication requires single-stranded DNA binding protein to avoid termination and production of double-stranded DNA. Nucleic Acids Res. 2014;42(16):10596-604. doi: 10.1093/nar/gku737. Epub Aug. 12, 2014.

Genot et al., Remote Toehold: A Mechanism for Flexible Control of DNA Hybridization Kinetics. J. Am. Chem. Soc. 2011:133(7):2177-82.

Gevensleben et al., Noninvasive detection of HER2 amplification with plasma DNA digital PCR. Clin Cancer Res. Jun. 15, 2013;19(12):3276-84. doi:10.1158/1078-0432.CCR-12-3768. Epub May 1, 2013.

Gilbert, et al., DNA replication: the rolling circle model. Cold Spring Harb Symp Quant Biol. 1968;33:473-84.

Gu et al., Small, highly active DNAs that hydrolyze DNA. J Am Chem Soc. Jun. 19, 2013;135(24):9121-9. doi: 10.1021/ja403585e. Epub Jun. 6, 2013.

Hogberg et al., Folding DNA origami from a double-stranded source of scaffold. J Am Chem Soc. Jul. 8, 2009; 131(26): 9154-9155. doi:10.1021/ja902569x.

Inoue et al., Improvements of rolling circle amplification (RCA) efficiency and accuracy using Thermus thermophilus SSB mutant protein. Nucleic Acids Res. May 17, 2006;34(9):e69.

Jungmann et al., Isothermal Assembly of DNA Origami Structures Using Denaturing Agents. J Am Chem Soc. Aug. 6, 2008;130(31):10062-3. doi: 10.1021/ja8030196. Epub Jul. 10, 2008.

Ke et al., Multilayer DNA Origami Packed on a Square Lattice. J Am Chem Soc. Nov. 4, 2009;131(43):15903-8. doi: 10.1021/ja906381y.

Ke et al., Self-assembled water-soluble nucleic acid probe tiles for label-free RNA hybridization assays. Science. Jan. 11, 2008;319(5860):180-3. doi: 10.1126/science.1150082.

Kinde et al., Detection and quantification of rare mutations with massively parallel sequencing. Proc Natl Acad Sci U S A. Jun. 7, 2011;108(23):9530-5. doi: 10.1073/pnas.1105422108. Epub May 17, 2011.

Li et al., A replicable tetrahedral nanostructure self-assembled from a single DNA strand. J Am Chem Soc. Sep. 16, 2009;131(36):13093-8. doi: 10.1021/ja903768f.

Li et al., Genotyping with TaqMAMA. Genomics. Feb. 2004;83(2):311-20.

Li et al., Replacing PCR with COLD-PCR enriches variant DNA sequences and redefines the sensitivity of genetic testing. Nat Med. May 2008;14(5):579-84. doi: 10.1038/nm1708. Epub Apr. 13, 2008.

Liedl et al., Self-assembly of three-dimensional prestressed tensegrity structures from DNA. Nat Nanotechnol. Jul. 2010;5(7):520-4. doi: 10.1038/nnano.2010.107. Epub Jun. 20, 2010.

Lin et al., Rolling circle enzymatic replication of a complex multi-crossover DNA nanostructure. J Am Chem Soc. Nov. 21, 2007;129(46):14475-81. Epub Oct. 27, 2007.

Liu et al., Pyrophosphorolysis-activated polymerization (PAP): application to allele-specific amplification. Biotechniques. Nov. 2000;29(5):1072-6, 1078, 1080 passim.

Lizardi et al., Mutation detection and single-molecule counting using isothermal rolling-circle amplification. Nat Genet. Jul. 1998;19(3):225-32.

Morgan et al. Characterization of the specific DNA nicking activity of restriction endonuclease N.BstNBI. Biol Chem. Nov. 2000;381(11):1123-5.

Newman at al., An ultrasensitive method for quantitating circulating tumor DNA with broad patient coverage. Nat Med. May 2014;20(5):548-54. doi: 10.1038/nm.3519. Epub Apr. 6, 2014.

Newton et al., Analysis of any point mutation in DNA. The amplification refractory mutation system (ARMS). Nucleic Acids Res. Apr. 11, 1989;17(7):2503-16.

Nilsson, M., et al. Padlock probes: circularizing oligonucleotides for localized DNA detection. Science. Sep. 30, 1994;265(5181):2085-8.

Orum et al., Single base pair mutation analysis by PNA directed PCR clamping. Nucleic Acids Res. Nov. 25, 1993;21(23):5332-6.

Rothemund, Folding DNA to create nanoscale shapes and patterns. Nature. Mar. 16, 2006;440:297-302.

Santalucia JR et al., The thermodynamics of DNA structural motifs. Annu Rev Biophys Biomol Struct. 2004;33:415-40.

Seyama et al., A novel blocker-PCR method for detection of rare mutant alleles in the presence of an excess amount of normal DNA. Nucleic Acids Res. May 25, 1992;20(10):2493-6.

Shih et al., A 1.7-kilobase single-stranded DNA that folds into a nanoscale octahedron. Nature. Feb. 12, 2004;427(6975):618-21.

Shih et al., Biomolecular assembly: dynamic DNA. Nat Mater. Feb. 2008;7(2):98-100. doi: 10.1038/nmat2110.

Shih et al., Knitting complex weaves with DNA origami. Current Opinion in Structural Biology. Jun. 2010;20(3):276-82. Author manuscript available in PMC Jun. 1, 2011.

Thomas et al., Amplification of padlock probes for DNA diagnostics by cascade rolling circle amplification or the polymerase chain reaction. Arch Pathol Lab Med. Dec. 1999;123(12):1170-6.

(56) References Cited

OTHER PUBLICATIONS

Wang et al. Site-selective DNA hydrolysis induced by a metal-free peptide nucleic acid-cyclen conjugate. Chem Commun. 47, 11059-11061, 2011.

Yin et al., Programming DNA tube circumferences. Science. Aug. 8, 2008;321(5890):824-6.

Yurke et al., A DNA-fuelled molecular machine made of DNA. Nature. Aug. 10, 2000;406(6796):605-8.

Zhang et al., Dynamic DNA nanotechnology using strand-displacement reactions. Nat Chem. Feb. 2011;3(2):103-13. doi: 10.1038/nchem.957.

Zhang et al., Optimizing the specificity of nucleic acid hybridization. Nat Chem. Jan. 22, 2012;4(3):208-14. doi: 10.1038/nchem.1246.

Zhou et al., Enrichment and detection of rare alleles by means of snapback primers and rapid-cycle PCR. Clin Chem. May 2010;56(5):814-22. doi: 10.1373/clinchem.2009.142034. Epub Mar. 18, 2010.

Zhang et al., Control of DNA strand displacement kinetics using toehold exchange. J Am Chem Soc. Dec. 2, 2009;131(47):17303-14.

Zhou et al., Rare allele enrichment and detection by allele-specific PCR, competitive probe blocking, and melting analysis. BioTechniques. May 2011; 50(5): 311-318.

\* cited by examiner

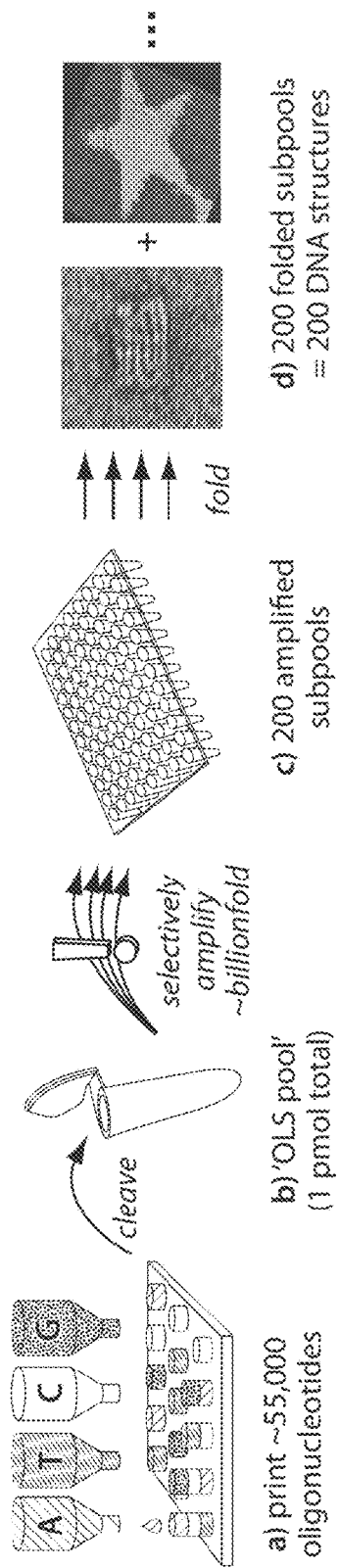

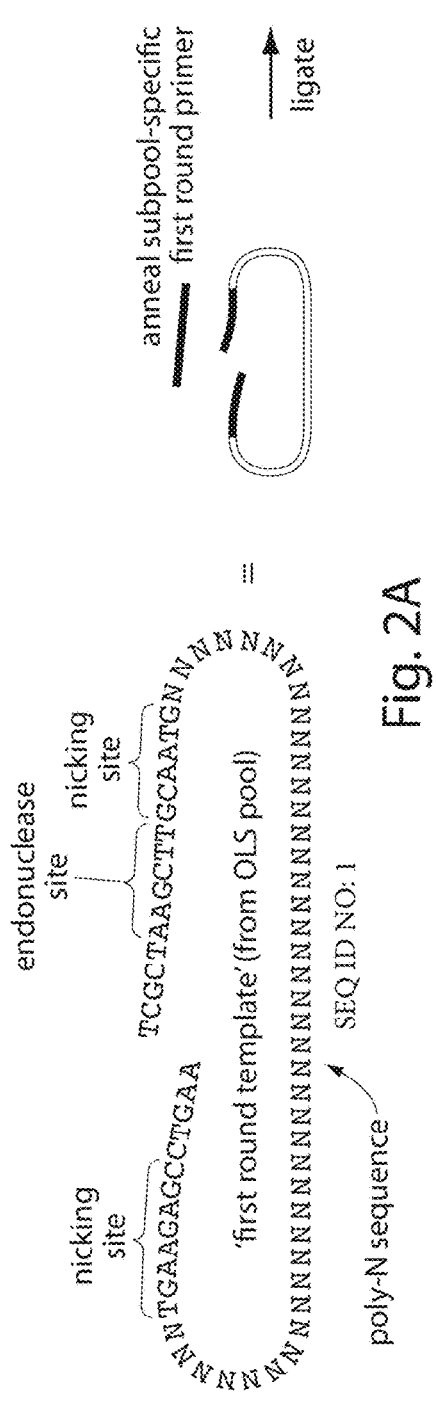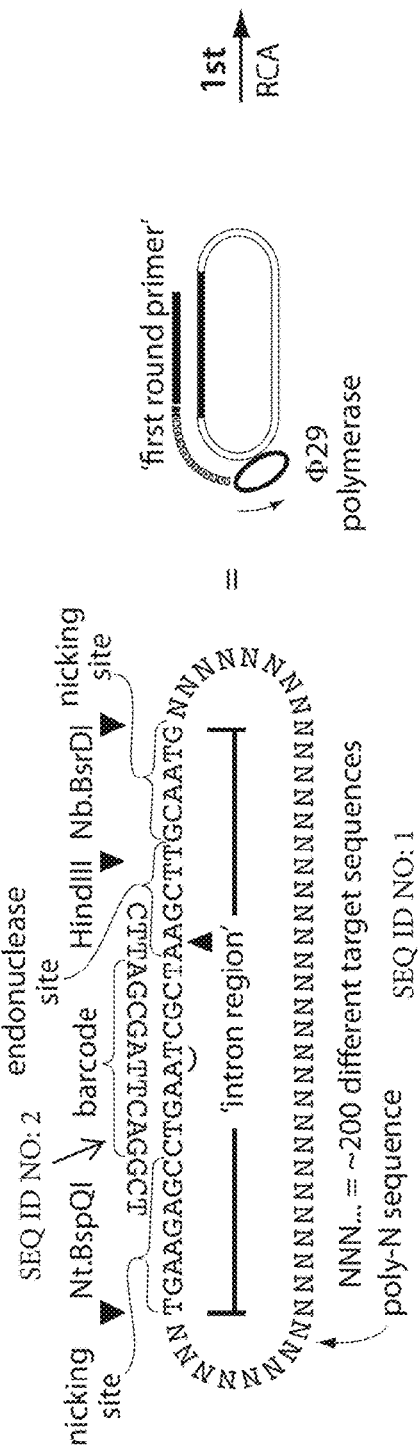
Fig. 2A
Fig. 2B

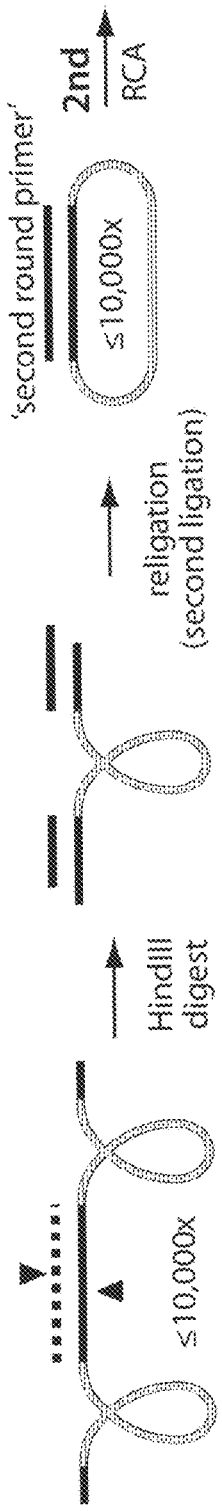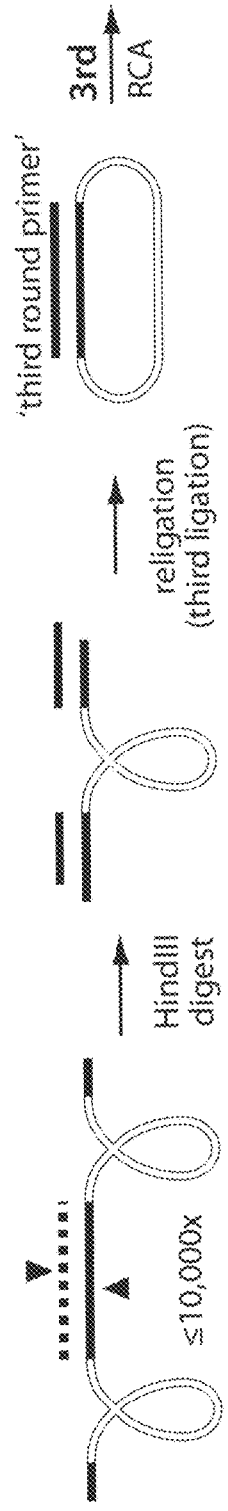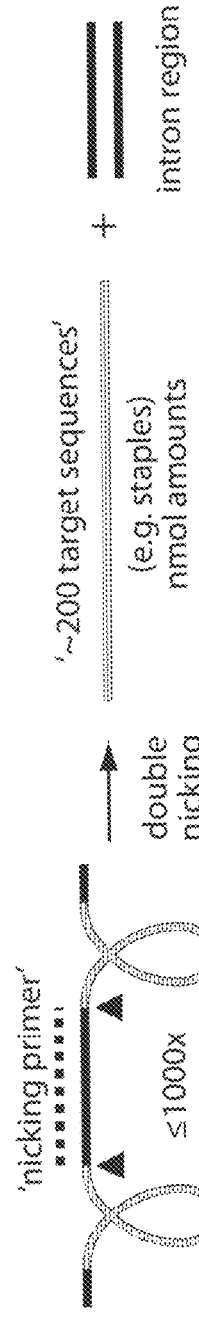

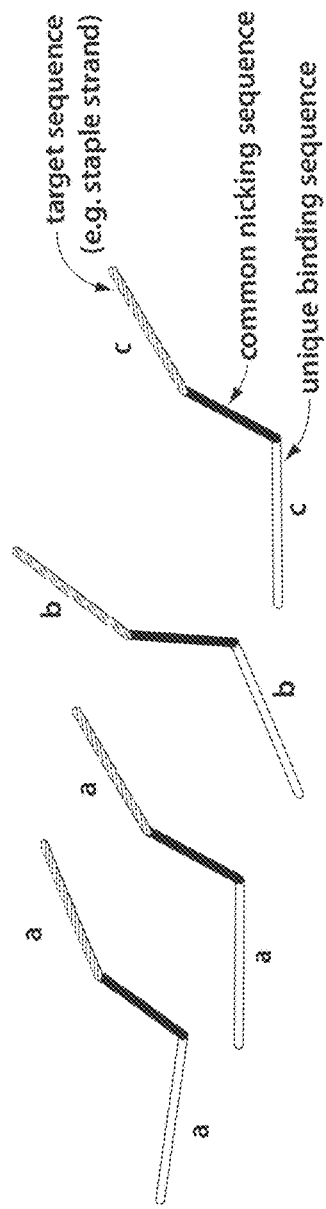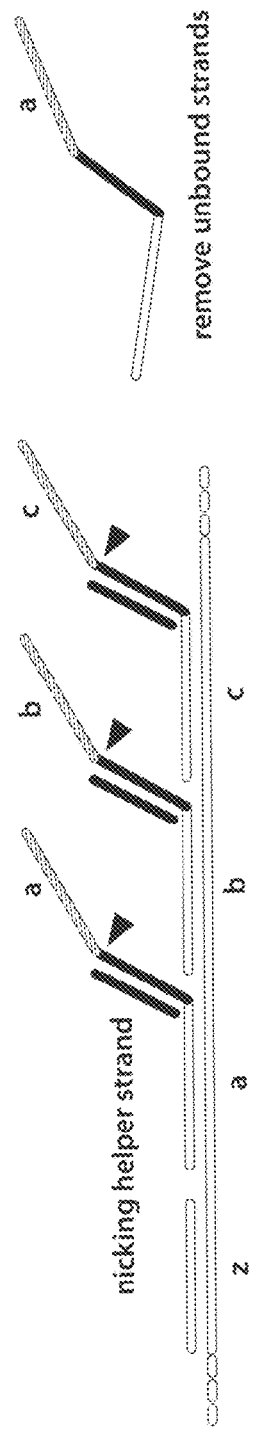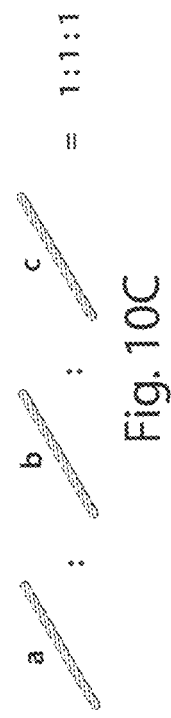

SEQUENCE LISTING

```
<160> NUMBER OF SEQ ID NOS: 8

<210> SEQ ID NO 1
<211> LENGTH: 72
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(59)
<223> OTHER INFORMATION: n is a, c, g, or t

<400> SEQUENCE: 1
tcgctaagct tgcaatgnnn nnnnnnnnnn nnnnnnnnnn nnnnnnnnnn nnnnnnnnnt    60
```
gaagagcctg aa                                                              72

<210> SEQ ID NO 2
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 2
cttagcgatt caggct                                                          16

<210> SEQ ID NO 3
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 3
tcgctaagct tgcaatggca gtcagagata cgacttatac aaccgagatt agtagtgcct          60
gaagagcctg aa                                                              72

<210> SEQ ID NO 4
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 4
gtcacaagct ttccgtttgt tgcaatggca gtcagagata cgacttatac aaccgagatt          60
agtagtgcct gaagagccaa ag                                                   82

<210> SEQ ID NO 5
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 5
aacaaacgga aagcttgtga cctttg                                               26

<210> SEQ ID NO 6
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (53)..(54)
<223> OTHER INFORMATION: n is a, c, g, or t

<400> SEQUENCE: 6
taacaggatt agcagagcga ggtgaagagc ctgaatcgct aagcttgcaa tgnn               54

<210> SEQ ID NO 7
<211> LENGTH: 41
<212> TYPE: DNA
<213> ORGANISM: Artificial Sequence
<220> FEATURE:
<223> OTHER INFORMATION: Synthetic Polynucleotide
<220> FEATURE:

```
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (37)..(41)
<223> OTHER INFORMATION: n is a, c, g, or t

<400> SEQUENCE: 7
nnnnnncatt gcaagcttag cgattcaggc tcttcannnn n                    41

<210> SEQ ID NO 8
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 8
cctcgctctg ctaatcctgt tattttttt                                  30
```

SELECTIVE NUCLEIC ACID AMPLIFICATION FROM NUCLEIC ACID POOLS

RELATED APPLICATIONS

This application is a national stage filing under 35 U.S.C. §371 of international PCT application PCT/US2013/025246, filed Feb. 8, 2013, which was published under PCT Article 21(2) in English and claims the benefit under 35 U.S.C. §119(e) of U.S. provisional application Ser. No. 61/596,821, filed Feb. 9, 2012, each of which is herein incorporated by reference in its entirety.

FIELD OF THE INVENTION

Embodiments described herein relate to the fields of genetic and molecular biology.

BACKGROUND OF THE INVENTION

Two- and three-dimensional nanoscale shapes can be constructed from folding a long strand of DNA. This folding is based on the specificity of the interactions between complementary nucleotides. Folding of the long DNA strand is aided by multiple short oligonucleotides, referred to as "staple" strands. Each oligonucleotide binds the longer DNA strand in multiple non-contiguous regions, resulting in various shapes. To produce a single shape such as a nanotube or nanosheet, hundreds (or even thousands) of select oligonucleotide staple strands may be required.

Tens of thousands of high-quality oligonucleotides (oligonucleotide pool) can be synthesized in parallel on chip-based platforms. Nonetheless, the amount of oligonucleotides (e.g., 1 pmol total) is far too small to be used directly for the assembly of two- and three-dimensional nanoscale nucleic acid structures.

SUMMARY OF THE INVENTION

The invention provides compositions and methods for generating sufficient amounts of high-quality oligonucleotides from an oligonucleotide pool. More specifically, the invention provides nucleic acids and methods of their use for selective amplification of oligonucleotides from a larger oligonucleotide pool, as well as the resultant oligonucleotide pools and subpools. Embodiments of the invention are based, at least in part, on a nucleic acid amplification method, referred to as rolling circle replication. The resultant oligonucleotides are suitable, inter alia, as staple strands in a DNA folding process (e.g., to generate DNA nanostructures), as probes for fluorescent in situ hybridization (FISH), as primers for targeted sequencing, as oligonucleotides for gene and genome synthesis, etc.

In one aspect, the invention provides a single-stranded nucleic acid comprising (a) a target sequence, (b) a 5' end having a first sequence, and (c) a 3' end having a second sequence such that when the 5' end and the 3' end are juxtaposed, the first sequence and the second sequence form a subpool-specific region, wherein the subpool-specific region (1) comprises a subpool-specific sequence and an endonuclease site, and (2) is flanked at each end by a nicking site.

In another aspect, the invention provides a circular nucleic acid comprising a single-stranded region and a double-stranded region, wherein the single-stranded region contains a target sequence, and wherein the double-stranded region (1) comprises a subpool-specific sequence and an endonuclease site, and (2) is flanked at each end by a nicking site.

A target sequence described herein may be but is not limited to about 15 to about 100 nucleotides in length, including about 25 to about 50 nucleotides in length.

In some embodiments, a double-stranded region may be about 8 to about 50 nucleotides in length.

In some embodiments, a subpool-specific sequence is about 8 to about 20 nucleotides in length.

In some embodiments, a 5' end and a 3' end of a single-stranded nucleic acid may be juxtaposed or covalently linked.

In some embodiments, a circular nucleic acid may be comprised of a first strand and a second strand, wherein the first strand has its 5' and 3' ends juxtaposed and hybridized to the second strand.

In some embodiments, a single-stranded nucleic acid or a circular nucleic acid may be hybridized, at the subpool-specific sequence, to an oligonucleotide of about 8 to about 20 nucleotides in length.

In some embodiments, a subpool-specific region comprises at least two subpool-specific sequences, each subpool-specific sequence comprising an endonuclease site.

In some embodiments, the double-stranded region of a circular nucleic acid may comprise at least two subpool-specific sequences, each subpool-specific sequence comprising an endonuclease site.

In some embodiments, an endonuclease site of a single-stranded nucleic acid or a circular nucleic acid may be unique (i.e., it is present only once in the single-stranded nucleic acid or the circular nucleic acid).

In some embodiments, the nicking sites of any one of the single-stranded nucleic acids or circular nucleic acids described herein may be the same or different.

In yet another aspect, the invention provides a plurality of any of the single-stranded or circular nucleic acids according to any one of the embodiments described herein.

In some embodiments, a plurality of these nucleic acids, including the single-stranded nucleic acids, comprises at least two subpools of single-stranded (or partially single-stranded) nucleic acids, each subpool having a unique subpool-specific sequence. In some embodiments, the plurality comprises at least five subpools or at least ten subpools of single-stranded nucleic acids, each subpool having a unique subpool-specific sequence. In some embodiments, the plurality comprises at least 20, at least 30, a least 40, at least 50, at least 100, at least 150, or at least 200 subpools of nucleic acids, each subpool having a unique subpool-specific sequence.

Target sequences within a subpool may be different between nucleic acids. In some embodiments, each subpool may comprise but is not limited to 1 to 1000 different target sequences, including at least 10, at least 20, at least 30, at least 40, at least 50, at least 100, at least 150, at least 200, at least 300, at least 400, at least 500 or more different target sequences within a subpool.

In some embodiments, the target sequences within the subpool may be of the same length. In some embodiments, the target sequences within the subpool may be of different lengths. In some embodiments, the target sequences within the pool may be of the same length. In some embodiments, the target sequences within the pool may be of different lengths.

In some embodiments, a target sequence may be a nucleotide sequence of a primer used in targeted sequencing, or of an oligonucleotide used for gene and/or genome synthesis, or as a probe for FISH.

In some embodiments, a target sequence may be a nucleotide sequence of an oligonucleotide used for a DNA folding process (e.g., a DNA staple strand). In some embodiments, one subpool of single-stranded nucleic acids may be sufficient to form a nucleic acid (e.g., DNA) nanostructure when combined with and hybridized to a longer nucleic acid (scaffold) strand. In some embodiments, five or ten subpools may be sufficient to form a nucleic acid (e.g., DNA) nanostructure when combined with a scaffold strand.

In some embodiments, a nucleic acid (e.g., DNA) nanostructure may be selected from the group consisting of a hemi-sphere, a cube, a cuboidal, a tetrahedron, a cylinder, a cone, an octahedron, a prism, a sphere, a pyramid, a dodecahedron, a tube, an irregular shape, and an abstract shape.

In another aspect, the invention provides a composition comprising a plurality of the afore-mentioned single-stranded nucleic acids in the presence of a kinase enzyme and/or kinase buffer. In some embodiments, the kinase enzyme is T4 kinase enzyme.

In another aspect, the invention provides a composition comprising a plurality of the afore-mentioned single-stranded nucleic acids in the presence of a ligase enzyme. In some embodiments, the ligase enzyme is T4 ligase enzyme. In some embodiments, the composition further comprises single-stranded primers specific for the subpool-specific sequences of the single-stranded nucleic acids. In some embodiments, the composition comprises circular nucleic acids that are partially double-stranded and partially single-stranded.

In another aspect, the invention provides a composition comprising a plurality of the afore-mentioned single-stranded or partially single-stranded nucleic acids, including circular nucleic acids, in the presence of a polymerase and/or dNTPs and/or a single-stranded primer that is specific for the subpool-specific sequence. In some embodiments, the single-stranded primer is a plurality of single-stranded primers, each having specificity for a different subpool-specific sequence. In some embodiments, the single-stranded primer is a plurality of single-stranded primers having identical specificity for subpool-specific sequences. In some embodiments, the composition comprises a single-stranded primer for each of a plurality of subpools of single-stranded or partially single-stranded nucleic acids including circular nucleic acids. In some embodiments, the polymerase is a DNA polymerase such as but not limited to Phi 29 polymerase. In some embodiments, the dNTPs are detectably labeled with for example radioisotopes or other detectable moieties. The dNTPs may be naturally or non-naturally occurring dNTPs provided they can be incorporated into a newly synthesized nucleic acid.

In another aspect, the invention provides a composition comprising isolated target sequences and isolated intron sequences, wherein the isolated intron sequences comprise subpool-specific sequences, and/or nicking sites and/or endonuclease site(s) (including any combination thereof). In some embodiments, the isolated target sequences are single stranded. In some embodiments, the isolated intron sequences are double-stranded. In some embodiments, composition comprises a nicking enzyme. In some embodiments, the composition comprises at least 50, at least 100, at least 150, at least 200, at least 250, or more different isolated target sequences. In some embodiments, the target sequences are present in nanomolar amounts or micromolar amounts. In some embodiments, the target sequences are present in equimolar amounts (relative to each other). In some embodiments, the composition comprises identical isolated intron sequences.

In another aspect, the invention provides a plurality of nucleic acids each comprising a target sequence, a nicking sequence, and a binding sequence. The target sequence may or may not be shared with other nucleic acids. The binding sequence may or may not be shared with other nucleic acids. The target sequences and the binding sequences however may be paired such that all nucleic acids having a particular target sequence (defined by nucleotide sequence) also have a particular binding sequence (defined by nucleotide sequence). Nucleic acids that differ in their target sequences will also differ in their binding sequences. The nicking sequence may be identical between nucleic acids (and may be referred to as "common"). In some embodiments, the composition further comprises nicking helper strands capable of hybridizing in a sequence-specific manner to the common nicking sequences (and thus specific for such sequences). In some embodiments, the composition further comprises helper scaffolds comprising a plurality of sequences complementary to the binding sequences of the shorter nucleic acids described above. In some embodiments, the helper scaffolds are present in a sub-stoichiometric amount. In some embodiments, a subset of nucleic acids is hybridized to the helper scaffolds, and optionally a subset of unhybridized nucleic acids is present. In some embodiments, the composition comprises a subset of nucleic acids hybridized to the helper scaffolds without excess unhybridized nucleic acids present. In another aspect, the invention provides a method of isolating target sequences from such helper scaffolds by nicking the target sequence from the hybridized complexes, and optionally physically separating the remainder of the hybridized complexes from the released target sequences. Thus, in yet another aspect, the invention provides a composition of isolated target sequences of equimolar amounts, optionally in the presence of helper scaffolds.

In one aspect, the invention provides a method comprising (a) contacting a plurality of single-stranded nucleic acids of any one of the embodiments described herein with ligase in the presence of a first primer that hybridizes to a subpool-specific sequence formed by juxtaposition of the 5' end and the 3' end of a single-stranded nucleic acid; (b) amplifying the single-stranded nucleic acids from the first primer via rolling circle replication to produce a first plurality of concatemers; (c) contacting the first plurality of concatemers with a second primer that hybridizes to the subpool-specific sequence and digesting the first plurality of concatemers with an endonuclease to produce a first plurality of monomers; (d) contacting the first plurality of monomers with ligase in the presence of the second primer; (e) amplifying the first plurality of monomers from the second primer via rolling circle replication to produce a second plurality of concatemers; (f) contacting the second plurality of concatemers with a third primer that hybridizes to the subpool-specific sequence and digesting the second plurality of concatemers with an endonuclease to produce a second plurality of monomers; (g) contacting the second plurality of monomers with ligase in the presence of the third primer; and (h) amplifying the second plurality of monomers from the third primer via rolling circle replication to produce a third plurality of concatemers.

The invention further provides methods comprising steps (a) and (b), (a) through (c); (a) through (d); (a) through (e); (a) through (f); or (a) through (g).

Some embodiments may further comprise nicking the third plurality of concatemers to produce a plurality of oligonucleotides consisting of the target sequence.

The methods of the invention may be performed in solution or on a solid support to which at least one of the nucleic acids is attached either directly or indirectly.

Some embodiments may further comprise hybridizing the plurality of oligonucleotides with a nucleic acid scaffold strand to produce a nucleic acid (e.g., DNA) nanostructure.

In another aspect, the invention provides a kit comprising a single-stranded nucleic acid, a circular nucleic acid, or a plurality of single-stranded nucleic acids of any one of the embodiments described herein. In some embodiments, the kit may further comprise instructions for amplifying the single-stranded nucleic acid, the circular nucleic acid, or the plurality of single-stranded nucleic acids. In some embodiments, the kit may comprises instructions for assembling a two- or three-dimensional DNA nanostructure.

In another aspect, the invention provides a composition comprising a single-stranded target nucleic acid having a having a target sequence, a common nicking sequence and a unique binding sequence; a single-stranded nicking helper strand having a sequence complementary to the common nicking sequence of the first single-stranded nucleic acid; and a single-stranded helper scaffold having a sequence complementary to the unique binding sequence of the target nucleic acid. In some embodiments, the composition comprises a plurality of the target nucleic acids, the nicking helper strands and the helper scaffolds, wherein each of the helper scaffolds has sequences complementary to two or more of the unique binding sequences.

In another aspect, the invention provides a method comprising combining in a single reaction (a) a single-stranded target nucleic acid having a having a target sequence, a common nicking sequence and a unique binding sequence, (b) a single-stranded nicking helper strand having a sequence complementary to the common nicking sequence of the first single-stranded nucleic acid, and (c) a single-stranded helper scaffold having a sequence complementary to the unique binding sequence of the target nucleic acid for a time sufficient to permit annealing, thereby forming a first double-stranded region between the target nucleic acid and the nicking helper strand and forming a second double-stranded region between the target nucleic acid and the helper scaffold; and adding to the reaction an enzyme that cleaves the first double-stranded region, thereby releasing the target sequence. In some embodiments, the single-stranded target nucleic acid is a plurality of the target nucleic acids, the single-stranded nicking helper strand is a plurality of nicking helper strands and the single-stranded helper scaffold is a plurality of helper scaffolds, wherein each of the helper scaffolds has sequences complementary to two or more of the unique binding sequences.

BRIEF DESCRIPTION OF THE DRAWINGS

FIG. 1 is a schematic representation of the synthesis of DNA nanostructures from one oligonucleotide pool (OLS-pool). (A) An oligonucleotide library with up to 55,000 different oligonucleotides is synthesized and cleaved off a chip. (B) From this OLS pool, subpools are selectively amplified by a circle-to-circle amplification about one billion-fold. (C) After the amplification reaction, each subpool (e.g., each well of a 96-well plate) contains staple strands for one specific structure. (D) Each subpool can be used to make one DNA origami structure. The first (TEM) image was taken of a test structure made using the enzymatically produced oligonucleotides described herein. The second (AFM) image is from Rothemund, et al., *Nature,* 440: 297-302 (2006).

FIGS. 2A-2E are schematics of the nucleic acids and nucleic acid amplification methods of the invention. (A) The linear template strands of a subpool are annealed with a subpool-specific first round primer. This primer does not bind to other subpools. The targeted template strands are ligated into circular template strands. (B) (left) shows the elements of the circular template. The poly-N sequence is the variable region. The nicking sites, the barcode sequence and the endonuclease site are indicated. The triangles represent the nicking/restriction sites. The "intron region" comprises all non-target sequences. A strand displacement polymerase synthesizes concatemerized copies of the circular template. (C) A "second round primer" is hybridized to the intron region of the first concatemer and the resulting double stranded region is digested with a restriction enzyme into monomers. After a heat denaturation step, excess second round primer hybridizes to the monomers and monomers are re-ligated. A second rolling circle reaction is performed. (D) A second concatemer: HindIII digest, re-ligation, and rolling circle amplification are repeated. (E) A third concatemer: a nicking primer (which, in some embodiments, can be identical to the second round primer) is hybridized to this concatemer. A double nicking reaction excises the intron region and the target sequences are purified.

FIGS. 7A-7C are schematic representations of a DNA affinity column workup of the final double nicking digestion reaction using extended nicking primers. (A) A nicking primer (grey in the schematic representation) was extended by 22 nucleotides (indicated as the extension sequence) and 2 degenerate nucleotides on the 3' end. The extension sequence stayed single-stranded during the nicking reaction. The two nicking enzymes cleaved the third round concatemer between the bases indicated with the triangles. (B) A schematic representation of the DNA affinity column with a sequence complementary to the single-stranded overhang on the nicking helper strand. The sequence also carries a T(8) linker. The sequence was synthesized on a DNA synthesis column with a non-cleavable solid support (arrow). (C) A representation of the nicking reaction workup. The extension of the nicking helper strand hybridized to the sequence on the non-cleavable support. The column retained the excess of the nicking helper strands, the common sequences of the nicking reactions, and eventual partially nicked products. Only the correctly nicked target sequences (bottom) were not retained by the affinity column and could be collected in the flow-through.

FIGS. 10A-10C are schematics of nucleic acids and nucleic acid amplification methods of the invention. (A) Target sequences (e.g., staple strands for a DNA origami, dark gray) are extended by common nicking sequences (light gray) and unique binding sequences (medium gray). (B) The unique binding sequences anneal to a sub-stoichiometric amount of a long single-stranded helper scaffold (medium gray, bottom). Unbound excess strands (right) are removed, for example, by PEG precipitation. Unused scaffold may be annealed to additional oligonucleotides (z) used to open up eventual secondary structures in the helper scaffold, and thus make the binding sites for the amplified oligonucleotides (a-c) fully accessible. The target strands are cleaved off by addition of nicking helper strands (light gray) and a restriction enzyme. (C) Recovered target sequences, A, B and C, are present in equimolar ratios.

DESCRIPTION OF THE INVENTION

Figure 3A:
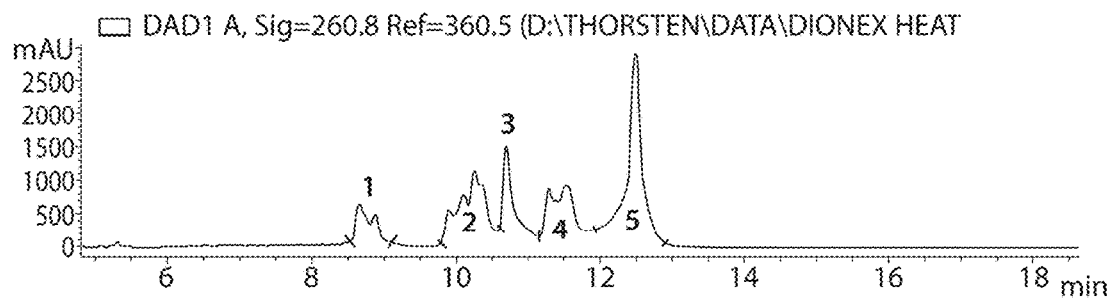
FIG. 3A shows an anion exchange chromatogram of the crude product of a final double nicking reaction, which was used to amplify staple strands of two different lengths. The fractions were collected as marked in the chromatogram. Fractions 2 and 4 contained 37 µg oligonucleotides total.

Tens of thousands of high quality oligonucleotides can be synthesized inexpensively in parallel on chips. In principle, hundreds of different nucleic acid (e.g., DNA) nanostructures of varying size, including those that are twice as large as those reported in the art, can be assembled from such an oligonucleotide (OLS) pool. Nonetheless, the quantity of oligonucleotides that is achievable "on-chip" (e.g., 1 pmol total or 18 amol per 55,000 different oligonucleotides) is not large enough to be used directly. Moreover, in the case of DNA origami, if several nucleic acid structures are synthesized in parallel, a background of unwanted oligonucleotides could negatively interfere with the nucleic acid folding process. It is thus advantageous in some instances to selectively amplify a subset of a few hundred oligonucleotides for a given structure for this particular application.

The DNA synthesis/amplification methods described herein have advantages over conventional methods. One advantage is a lower production cost. Conventional DNA synthesis on columns typically requires synthesis of oligonucleotides "one-by-one," which can be both costly and inefficient (e.g., it can cost as much as about $0.10 per nucleotide, or about $700 to synthesize all the oligonucleotides necessary to assemble a single DNA nanostructure). By comparison, the methods provided herein may employ chip-based synthesis of oligonucleotides to synthesize thousands of oligonucleotides (≤200-mers) in parallel, costing a fraction of the price (e.g., it can cost about $0.05 per nucleotide, or about $3.5 to synthesize all the oligonucleotides necessary to assemble a single DNA nanostructure). Another advantage of the methods provided herein is the high quality of oligonucleotides. Conventionally synthesized oligonucleotides typically contain many truncated sequences. The enzymatic methods described herein, in some embodiments, contain negligible amounts of truncations. A higher oligonucleotide quality will likely lead to fewer defects and better folding yields of nucleic acid nanostructures.

Thus, in some aspects, the invention provides nucleic acids and methods suitable for the selective amplification of arbitrary oligonucleotides from a chip-synthesized oligonucleotide pool. The methods are based, at least in part, on rolling circle replication and circle-to-circle amplification. Briefly, these methods use consecutive rounds (e.g., three consecutive rounds) of rolling circle replication to amplify a target sequence up to about a billion times for analytical purposes (Nilsson, M., et al. *Science*, 265: 2085-88 (1994); Dahl, F. et al., *Proc. Nat. Acad. Sci. U.S.A.*, 101(13): 4548-53 (2004), incorporated by reference herein in their entirety). In some embodiments, the methods described herein directly produce single-stranded oligonucleotides with arbitrary (or defined) sequences that differ from those found in existing protocols, such as those primers used in conventional polymerase chain reactions (PCRs).

In various aspects, the invention provides single-stranded nucleic acids having (1) a target sequence, (2) a 5' end having a first sequence, and (3) a 3' end having a second sequence such that when the 5' end and the 3' end are juxtaposed, the first sequence and the second sequence form a subpool-specific region, wherein the subpool-specific region (a) comprises a subpool-specific sequence and an endonuclease site and (b) is flanked on each end by a nicking site.

"Nucleic acid" or "oligonucleotide" as used herein refers to at least two nucleotides covalently linked together. The two terms may be used interchangeably herein. In some embodiments, the oligonucleotide may be less than 500, less 400, less than 300, less than 200, less than 100, or less than 50 nucleotides in length. A nucleic acid will generally contain phosphodiester bonds, although in some cases nucleic acid analogs are included that may have alternate backbones, comprising, for example, phosphoramide (Beaucage et al., *Tetrahedron* 49(10):1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al., *Chem. Lett.* 805 (1984), Letsinger et al., *J. Am. Chem. Soc.* 110: 4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996), all of which are incorporated by reference). Other analog nucleic acids include those with positive backbones (Denpcy et al., *Proc. Natl. Acad. Sci. USA* 92:6097 (1995); non-ionic backbones (U.S. Pat. Nos. 5,386,023, 5,637,684, 5,602,240, 5,216,141 and U.S. Pat. No. 4,469,863; Kiedrowshi et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, ASC Symposium Series 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins et al., *Chem. Soc. Rev.* pp. 169-76 (1995)). All of these references are hereby expressly incorporated by reference herein. These modifications of the ribose-phosphate backbone may be done to facilitate the addition of labels, or to increase the stability and half-life of such molecules in physiological environments.

The nucleic acids described herein may be single-stranded or double-stranded, as specified, or they may comprise both single-stranded and double-stranded regions. The nucleic acids may be DNA, both genomic and cDNA, RNA, or a hybrid, where the nucleic acids contain any combination of deoxyribo- and ribonucleotides, and any combination of bases, including uracil, adenine, thymine, cytosine, guanine, inosine, xathanine hypoxathanine, isocytosine, and isoguanine.

"Target sequence" as used herein refers to any nucleic acid sequence of interest, which can be isolated, synthesized, or amplified using standard molecular biology methods and/or those methods provided herein. A target sequence can be any length. In some embodiments, the target sequence is about 15 to about 100 nucleotides in length. In some embodiments the target sequence is about 25 to about 50 nucleotides in length. For example, in some embodiments, the nucleic acids and methods provided herein are used to amplify target sequences that will ultimately be used as "staple" strands for folding assembly of two- or three-dimensional nucleic acid nanostructures. Such staple strands are typically less than 100 nucleotides in length; however, they may be longer or shorter depending on the application. In some instances, multiple target sequences may be comprised within a single nucleic acid strand. In such instances, the multiple target sequences may be used to form a single DNA nanostructure.

A single-stranded non-circular nucleic acid (e.g., DNA) has two non-identical ends, the 3' end and the 5' end. The numbers refer to the numbering of carbon atoms in a deoxyribose, which is a sugar forming an important part of the backbone of the DNA molecule. In the backbone of DNA, for example, the 5' carbon of one deoxyribose is linked to the 3' carbon of another by a phosphate group. The 5' carbon of this deoxyribose is again linked to the 3' carbon of the next, and so forth. A 5' end and a 3' end of a linear nucleic acid are "juxtaposed" if they are adjacent (e.g., see FIG. 2A). Ends of a nucleic acid that are juxtaposed may or may not be covalently linked to each other. For example, in some embodiments, there may be a gap separating juxtaposed 5' and 3' ends.

A single-stranded circular nucleic acid refers to a nucleic acid that is configured into a circular shape. In some embodiments a circular nucleic acid is a contiguous nucleic acid, each nucleotide being covalently linked to an adjacent nucleotide, while in some embodiments a gap separates the 5' carbon of one deoxyribose from the 3' carbon of an adjacent deoxyribose. Thus, in some embodiments, a circular nucleic acid is formed by the juxtaposition of two ends of a linear nucleic acid, where the nucleotide at the 5' end and the nucleotide at the 3' may be positioned adjacent to each other but may not be covalently linked (FIG. 2A). As an example, the two ends of a first single-stranded nucleic acid may be held together in juxtaposition by a second (typically, linear single-stranded) nucleic acid that is hybridized (by sequence complementarity) to both the 5' end and the 3' end of the first single-stranded nucleic acid such that a circular structure is formed (FIG. 2B). This region of nucleic acid hybridization (complementarity) is referred to as a "double-stranded region" of a circular nucleic acid.

The invention contemplates pools and subpools of nucleic acids such as the single-stranded nucleic acids, circular nucleic acids, and "staple" oligonucleotides of the invention. A subpool of nucleic acids is a discrete population of nucleic acids within a larger population (pool) of nucleic acids. The pool and subpool may be heterogeneous. A heterogeneous pool may be subdivided into multiple heterogeneous subpools. A single subpool of nucleic acids, including staple oligonucleotides, may be defined by a particular end-product nanostructure, or part of a nanostructure, assembled using the oligonucleotides of that subpool. For example, a single subpool may contain all (or most of) the oligonucleotides necessary to assemble a DNA nanotube (or multiple copies of a DNA nanotube). In some embodiments, more than one subpool of oligonucleotides may be used to assemble a single type of DNA nanostructure. For example, part of the DNA nanostructure may be assembled using subpool A, while another part of the same DNA nanostructure may be assembled using subpool B. A "subpool-specific sequence" or "barcode" (used interchangeably herein) refers to a nucleic acid sequence that is unique to a particular subpool of nucleic acids (but shared among nucleic acids within the particular subpool). In some embodiments, a barcode may be comprised of shorter sequences, some of which are common to more than one barcode. For example barcode A and barcode B, while each unique, may share a common endonuclease site (e.g., HindIII) and/or nicking site. A barcode/subpool-specific sequence may be any desired length. For example, a barcode/subpool-specific sequence may be but is not limited to about 5 to about 300 nucleotides, or about 5 to about 200 nucleotides, or about 5 to about 100 nucleotides, or about 5 to about 50 nucleotides in length. In some embodiments, the length of the subpool-specific sequence is about 8 to about 20 nucleotides. In some embodiments, the length of the subpool-specific sequence is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 120, 140, 160, 180, 200, 220, 240, 260, 280 or 300 nucleotides in length (or more). In some embodiments, a subpool-specific sequence comprises an endonuclease site.

In some embodiments, a subpool may contain nucleic acids of differing sequence but of the same length.

In some embodiments, a subpool may contain nucleic acids of various lengths. For example, a subpool may contain nucleic acids of two different lengths. In some embodiments, a subpool may contain nucleic acids of 3, 4, 5, 6, 7, 8, 9, 10, 15, 20, or more, different lengths. Thus, the invention provides for the amplification and, in some instances, purification of complex mixtures of nucleic acids.

In some embodiments, a subpool may contain at least two nucleic acids of differing sequence but of the same length at least another nucleic acid that differs from the other nucleic acids in sequence and length.

A "subpool-specific region" or an "intron region" (used interchangeably herein) refers to a nucleic acid sequence (a) having a (e.g., one or more) subpool-specific sequences and an endonuclease site and (b) flanked on each end by a nicking site. A subpool-specific region may be but is not limited to about 10 to about 200 nucleotides in length. In some embodiments, the length of the subpool-specific region is about 50 or about 100 nucleotides in length. In some embodiments, the length of the subpool-specific region is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, or 300 or more nucleotides in length. In some embodiments, a subpool-specific region comprises two subpool-specific sequences. In some embodiments, each subpool-specific sequence comprises an endonuclease site (e.g., at its 5' or 3' end).

An "endonuclease site" as used herein refers to a nucleic acid sequence recognized and cleaved (cut) by a restriction endonuclease (enzyme). In some embodiments, the endonuclease site is unique to the nucleic acid. A nucleic acid having a unique endonuclease site refers to a nucleic acid that is cleaved only once by a corresponding endonuclease. For example, a circularized nucleic acid having a unique endonuclease site (e.g., AAGCTT) is linearized by a single cut from the corresponding endonuclease (e.g., HindIII). Examples of endonucleases include, but are not limited to, AatII, Acc65I, AccI, AciI, AclI, AcuI, AfeI, AflII, AflIII, AgeI, AgeI-HF™, AhdI, AleI, AluI, AlwI, AlwNI, ApaI, ApaLI, ApeKI, ApoI AscI, AseI, AsiSI, AvaI, AvaII, AvrII, BaeGI, BaeI, BamHI, BamHI-HF™, BanI, BanII, BbsI, BbvCI, BbvI, BccI, BceAI, BcgI, BciVI, BclI, BcoDI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaI-HF™, BsaJI, BsaWI, BsaXI, BseRI, BseYI, BsgI BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, BtsIMutI, Cac8I, ClaI, CspCI, CviAII, CviKI-1, CviQI, DdeI, DpnI, DpnII, DraI, DraIII, DraIII-HF™, DrdI, EaeI, EagI, EagI-HF™, EarI, EciI, Eco53kI, EcoNI, EcoO109I, EcoP15I, EcoRI, EcoRI-HF™, EcoRV, EcoRV-HF™, FatI, FauI, Fnu4HI, FokI, FseI, FspEI, FspI, HaeII, HaeIII, HgaI, HhaI, HincII, HindIII, HindIII-HF™, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, KpnI-HF™, LpnPI, MboI, MboII, MfeI, MfeI-HF™, MluCI, MluI, MlyI, MmeI MnlI, MscI, MseI, MslI, MspA1I, MspI, MspJI, MwoI, NaeI, NarI, NciI, NcoI, NcoI-HF™, NdeI, NgoMIV, NheI, NheI-HF™, NlaIII, NlaIV, NmeAIII, NotI, NotI-HF™, NruI, NsiI, NspI, Pad, PaeR7I, PciI, PflFI, PflMI, PhoI, PleI, PmeI, PmlI, PpuMI, PshAI, PsiI, PspGI, PspOMI, PspXI, PstI, PstI-HF™, PvuI, PvuI-HF™, PvuII, PvuII-HF™, RsaI, RsrII, SacI, SacI-HF™, SacII, SalI, SalI-HF™, SapI, Sau3AI, Sau96I, SbfI, SbfI-HF™, ScaI, ScaI-HF™, ScrFI, SexAI, SfaNI, SfcI, SfiI, SfoI, SgrAI, SmaI, SmlI, SnaBI, SpeI, SphI, SphI-HF™, SspI, SspI-HF™, StuI, StyD4I, StyI, StyI-HF™, SwaI, Taqαl, TfiI, TliI, TseI, Tsp45I, Tsp509I, TspMI, TspRI, Tth111I, XbaI, XcmI, XhoI, XmaI, XmnI, and ZraI. It is to be understood that the nucleic acids of the invention may comprise one or more sites recognized and cleaved by any of these enzymes.

A "nicking site" as used herein refers to a nucleic acid sequence recognized and cleaved (cut) by a nicking enzyme. Examples of nicking enzymes include, but are not limited to, Nb.BbvCI, Nb.BsmI, Nb.BsrDI, Nb.BtsI, Nt.AiwI, Nt.BbvCI, Nt.BsmAI, Nt.BspQI, Nt.BstNBI, and Nt.CviPII. In some embodiments the nicking sites are the same, and in some embodiments the nicking sites are different. For example, a nucleic acid may comprise two Nt.BspQI nicking sites, or a nucleic acid may comprise one Nt.BspQI nicking site and one Nb.BsrDI nicking site.

A "nucleic acid nanostructure" refers to a nanoscale object assembled using nucleic acids. The nucleic acid nanostructures of the invention include DNA nanostructures. It is to be understood that although certain exemplifications of the invention are described in terms of "DNA nanostructures," the invention is not so limited and the exemplifications are contemplated to include nucleic acid nanostructures more generally. A nucleic acid nanostructure may be two- or three-dimensional. Typical nucleic acid nanostructures have a spatial resolution of about 5 nm to about 50 nm, though the spatial resolution may be greater than 50 nm. In some embodiments, the nucleic acid nanostructures are DNA nanostructures.

In some aspects, the invention provides a circular nucleic acid having a single-stranded region and a double-stranded region. In some embodiments, the single-stranded region contains a target sequence (or the complement of a target sequence), and the double-stranded region contains a subpool-specific sequence and an endonuclease site and is flanked at each end by a nicking site. In some embodiments, the double stranded region forms part of a nicking site and/or an endonuclease site (see, e.g., FIG. 2B).

In other aspects, the invention provides a plurality of single-stranded nucleic acids, each nucleic acid having a target sequence, a 5' end having a first sequence, and a 3' end having a second sequence such that when the 5' end and the 3' end are juxtaposed, the first sequence and the second sequence form a subpool-specific region, wherein the subpool-specific region comprises a subpool-specific sequence and an endonuclease site and is flanked at each end by a nicking site.

In some embodiments, a plurality of nucleic acids comprises at least two subpools of single-stranded nucleic acids, each subpool having a unique subpool-specific sequence. For example, a plurality may comprise at least three, at least four, at least five, at least six, at least seven, at least eight, at least nine, or at least ten subpools of single-stranded nucleic acids. In some embodiments, a subpool may contain but is not limited to about 1 to about 1000 different target sequences. In some embodiments, a subpool may contain about 1 to about 900, about 1 to about 800, about 1 to about 700, about 1 to about 600, about 1 to about 500, about 1 to about 400, about 1 to about 300, about 1 to about 200, or about 1 to about 100 different target sequences. In some embodiments, a subpool may contain about 100 to about 1000, about 200 to about 1000, about 300 to about 1000, about 400 to about 1000, about 500 to about 1000, about 600 to about 1000, about 700 to about 1000, about 800 to about 1000, or about 900 to about 1000 different target sequences. In some embodiments, a subpool may contain more than 1000 different target sequences, depending on the application.

"Rolling circle replication" or "rolling circle amplification" (used interchangeably herein) refers to a process of unidirectional nucleic acid replication that can rapidly synthesize multiple copies of circular molecules of DNA or RNA (Gilbert, W. & Dressler, D. *Cold Spring Harbor Symp. Quant. Biol.,* 33: 473-484 (1968); Baker, T. A. & Kornberg, A. *DNA Replication* (Freeman, N.Y.) (1992)). Rolling circle replication proceeds in a linear fashion, and a highly processive DNA polymerase (e.g., Φ29 polymerase) can copy a 100-nucleotide circular probe into a DNA strand containing ~1,000 complements of the circularized molecule in 1 hour (Baner, J., et al. *Nucleic Acids Res.,* 26: 5073-78 (1998)). Such a DNA strand is referred to herein as a "concatemer." The amplification rate of rolling circle replication (RCR) has been improved by including a second primer, complementary to the RCR product, permitting replication of these products by a strand displacement mechanism, yielding a billion-fold amplification in an isothermal reaction in less than 1 hour (Lizardi, P., et al. *Nat. Genet.* 19:225-32 (1998)). To improve the quantitative sensitivity of this process, circular nucleic acids can be copied by RCR to generate single-stranded products composed of repeats of probe complements. In a series of reaction steps, the products are monomerized, converted to new nucleic acid circles, and used to template subsequent rounds of RCR. The reactions are repeated in a cyclical process where the polarity of the amplified nucleic acid alternates between cycles. Rolling circle amplification methods of the prior art do not permit selective amplification of nucleic acids from a larger pool.

In various aspects, the invention provides methods of selectively amplifying subpools of nucleic acids (e.g., oligonucleotides) from a larger pool. Such methods may include (a) contacting the plurality of single-stranded nucleic acids of any one of the embodiments described herein with ligase in the presence of a first primer that hybridizes to a subpool-specific sequence formed by juxtaposition of the 5' end and the 3' end of a single-stranded nucleic acid; (b) amplifying single-stranded nucleic acids hybridized to the first primer via rolling circle replication to produce a first plurality of concatemers; (c) contacting the first plurality of concatemers with a second primer that hybridizes to the subpool-specific sequence and digesting the first plurality of concatemers with an endonuclease to produce a first plurality of monomers; (d) contacting the first plurality of monomers with ligase in the presence of the second primer; (e) amplifying the first plurality of monomers hybridized to the second primer via rolling circle replication to produce a second plurality of concatemers; (f) contacting the second plurality of concatemers with a third primer that hybridizes to the subpool-specific sequence and digesting the second plurality of concatemers with an endonuclease to produce a second plurality of monomers; (g) contacting the second plurality of monomers with ligase in the presence of the third primer; (h) and amplifying the second plurality of monomers hybridized to the third primer via rolling circle replication to produce a third plurality of concatemers. The methods of the invention may comprise steps (a) through (h), (a) through (g), (a) through (f), (a) through (e), (a) through (d), (a) through (c), or (a) and (b).

In some embodiments, the methods described herein may further include nicking the third plurality of concatemers to produce a plurality of oligonucleotides consisting of the target sequence, without extraneous flanking nucleic acid sequence. A nicking enzyme is an enzyme that cuts one strand of a double-stranded nucleic acid at a specific recognition nucleotide sequence known as a restriction site. Such enzymes hydrolyze/cut only one strand of a double-stranded nucleic acid (e.g., DNA duplex) to produce nucleic acid molecules that are "nicked," rather than cleaved (Ando, T., et al. *J Biochem.* (1969) 66 (1): 1-10; Morgan. R. D., et al. *Biol Chem.* (2000) 381 (11): 1123-5).

FIG. 2 is a schematic representation of one embodiment of the inventive method. The reverse complement of an arbitrary DNA sequence (poly-N) is flanked by two nicking sites, a restriction site (endonuclease), and barcodes. The template strand is circularized with a splint or "first round primer." Next, a Phi-29 (Φ29) polymerase (oval) produces 1,000-10,000 complementary copies of the circularized template by rolling circle amplification (RCA). Second round primers are added to the concatemer and cut into monomers. These monomers are then self-ligated and each monomer serves as a template for a second round of RCA. The second round concatemer is cut and self-ligated, followed by a third round of RCA. The target sequence is cut out with two nicking enzymes to produce a target sequence with "clean" ends. After three rounds of circle-to-circle amplification, about a billion-fold of template strand may be obtained at high micromolar (µM) concentrations of the target sequence. This may be up to 100 times more than what is achieved by standard polymerase chain reaction.

The amplification conditions used herein may be similar to those described by, for example, Dahl, F. et al. (2004). In some embodiments, circular nucleic acids may be prepared by ligation of primers (e.g., 20 nm) in polymerase buffer (e.g., φ29 polymerase buffer: 50 mM Tris.HCl, pH 7.5, 10 mM MgCl2, 20 mM (NH4)2SO4, 0.2 µg/µl bovine serum albumin (BSA)) with ATP (e.g., 1 mM) and ligase (e.g., 0.02 units/µl T4 DNA ligase (New England Biolabs)) templated by target oligonucleotides (e.g., 60 nm) at 25° C. for about 10 min.

In some embodiments, circular nucleic acids may be replicated in polymerase buffer (e.g., φ29 polymerase buffer) with dNTPs (e.g., 1 mM) and polymerase (e.g., 3 units of φ29 polymerase, New England Biolabs) at 30° C. for 1 h. In such embodiments, additions may be made in volumes of 5 µl to an initial volume of 5 µl of primer ligation reaction. Replication reactions may be terminated by 10-min incubation at 65° C. To monomerize concatemer products, primers complementary to the replication sequence in the concatemer products may be added together with restriction enzyme (e.g., 10 units) in polymerase buffer, followed by incubation at 37° C. for 30 min. After monomerization, the enzyme may be inactivated at 65° C. for 10 min. The monomerized products may then be circularized by adding T4 DNA ligase (e.g., 1 unit) in polymerase buffer with ATP (e.g., 5 mM) and incubating for 5 min at 37° C. Polymerization, monomerization, and circularization may be further repeated, as desired. The concentration of primer for a first-generation monomerization reaction may be 0.1 µM, and it may be increased 3-fold for each subsequent monomerization reaction.

In some embodiments, a monomer product may be labeled, for example, radiolabeled or fluorescently labeled. As an example, circular nucleic acids may be amplified by any one of the methods described herein, but including, for example, 20 µCi [α-$^{32}$P]dCTP (3,000 mCi/mmol, Amersham Pharmacia; 1 Ci=37 GBq) in the amplification reactions. The products may be separated on a polyacrylamide gel with urea in buffer (e.g., TBE buffer: 45 mM Tris-borate, pH 8.3/1 mM EDTA), and the gel may be analyzed on a PhosphorImager (Fuji Bas-1800II).

A "primer" (also referred to as a "probe") refers to a short, single-stranded nucleic acid that is complementary to and hybridizes to another, typically longer, single-stranded nucleic acid. A primer may serves as a starting point for nucleic acid synthesis. A primer may be about 10 to about 100 nucleotides in length. In some embodiments, a primer is about 20, 30, 40, 50, 60, 70, 80, or 90 nucleotides in length. Some embodiments herein refer to the "polarity" of a primer. A primer is designated as having a (+) polarity, while its complement has a (−) polarity.

"Selective amplification" of or "selectively amplifying" a subpool of nucleic acids refers to a process by which a discrete population (subpopulation) of nucleic acids is replicated. As discussed in greater detail above, a subpool of nucleic acids may be defined by the end-product nanostructure assembled using the nucleic acids within the subpool together with a "scaffold" strand. Alternatively, a subpool may be arbitrarily defined, depending on the purpose of selective amplification.

"Contacting" reagents may be accomplished by combining or mixing the reagents, or adding a reagent to a solution comprising another reagent.

A "plurality" of nucleic acids as used herein refers to more than one nucleic acid. For example, a plurality of single-stranded nucleic acids may encompass as few as two nucleic acids or as many as a thousand, or more, nucleic acids.

A "concatemer" as used herein refers to a long continuous nucleic molecule that contains multiple copies of the same nucleic acid sequence, linked in series. For example, a concatemer may contain multiple copies of a target sequence or multiple copies of a sequence complementary to the target sequence. A "plurality of concatemers" as used herein refers to more than one concatemer, each containing multiple copies of a similar nucleic acid sequence.

A "monomer" refers to a single copy of a particular nucleic acid sequence. A monomer may be linear or circular. A concatemer contains multiple monomers. For example, a concatemer may contain multiple monomers of a target oligonucleotide sequence. A "plurality of monomers" as used herein refers to more than one monomer, each of a similar nucleic acid sequence.

A "first round primer" as used herein refers to a primer that is complementary to the barcode sequence on a starting nucleic acid and can also contain sequences complementary to the intron region. In some embodiments, the sequences of the barcodes are selected to form no or only weak secondary structures with the rest of the intron region. A "second round primer" includes a primer that contains at least the barcode and the endonuclease site. In some embodiments, a second primer can further contain one or more nicking sequences.

In some embodiments, a "third round primer" includes the reverse complement of the second round primer.

Figure 7A:
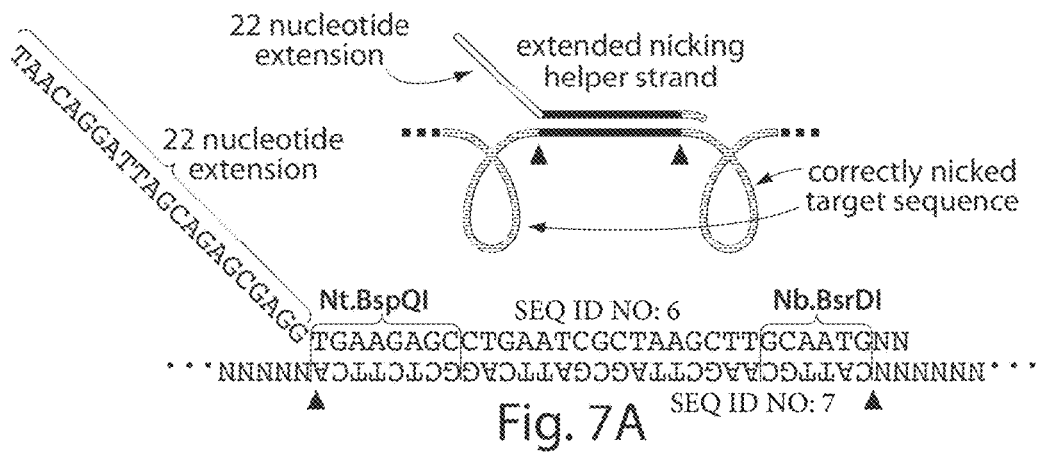
Figure 7B:
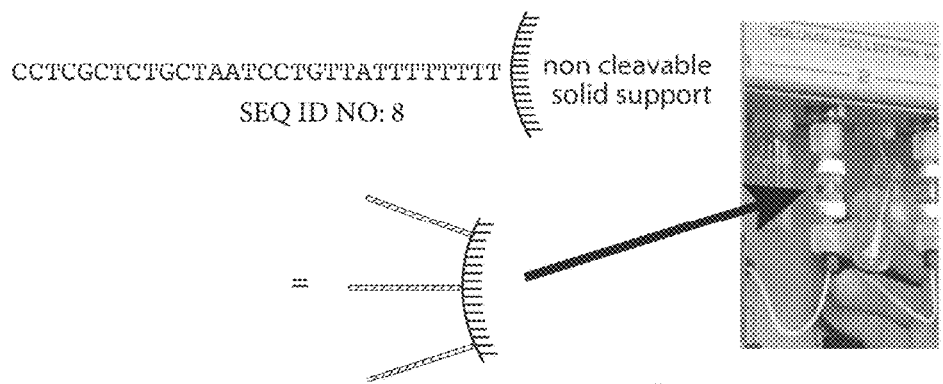
Figure 7C:
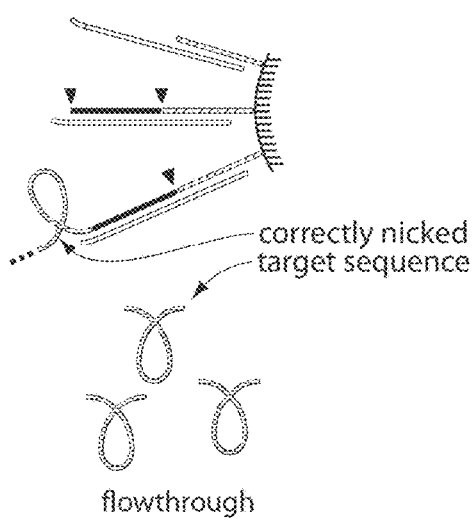
Figure 8A:
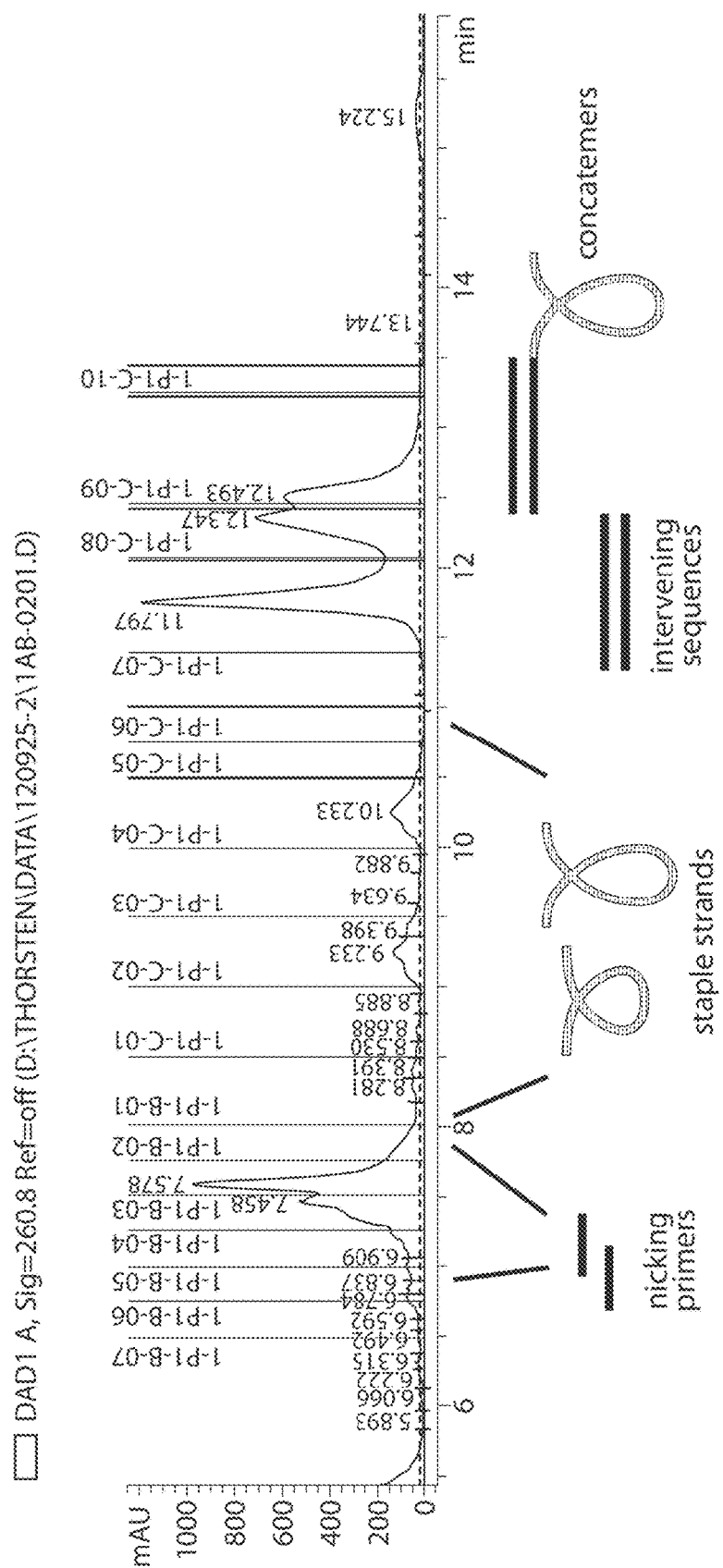
FIG. 8A shows an anion exchange high performance liquid chromatogram (HPLC) of the crude product of a final double nicking reaction, which was used to amplify staple strands of various lengths. The fractions were collected as marked by vertical lines in the chromatogram. The fractions collected between 8 and 11 minutes contain staple strands, which were pooled and concentrated.
Figure 8B:
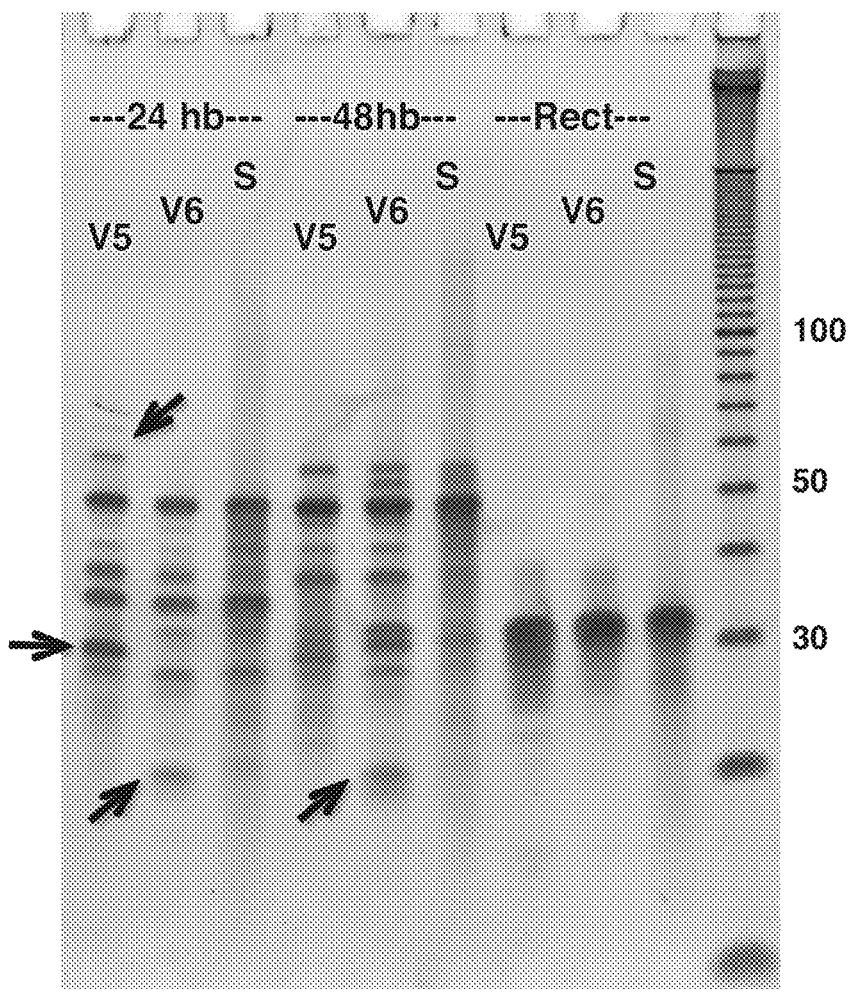
FIG. 8B shows a denaturing PAGE image of six pooled fractions collected from six different final double nicking reaction, each lane representing one of three different structures: a 24-helix bundle, a 48-helix bundle or a 2-dimensional rectangle. Oligonucleotide pools amplified with the barcode designs V5 (single barcode) and V6 (double barcode) were compared against a synthetically produced (S) commercial oligonucleotide pool (Integrated DNA Technologies Inc.). After the final double nicking reaction, the c2ca-amplified pools were purified by anion exchange high performance liquid chromatography (HPLC). The lower, light gray arrows point to residual nicking primers and/or intervening sequences. These nucleic acids do not affect the quality of folding. The top, dark gray arrow points to residual concatemers, which are present due to inadvertently including an incorrect fraction after anion-exchange chromatography.
Figure 9A:
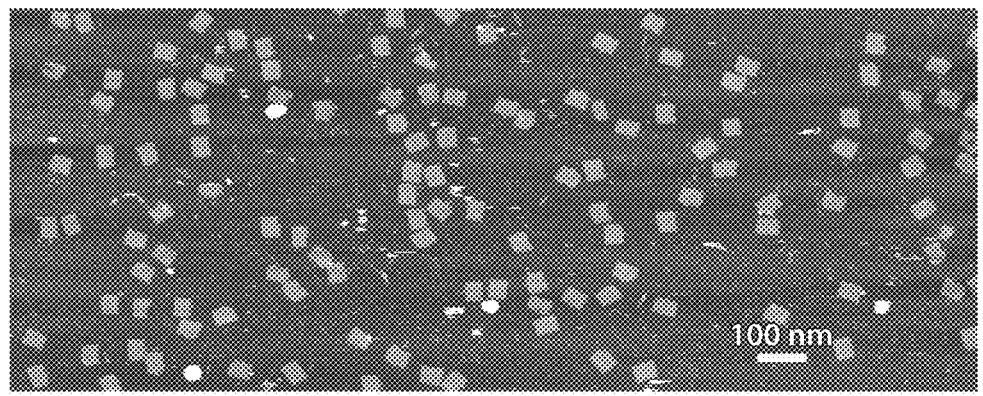
FIGS. 9A-9C are images of three different DNA nanostructures folded with enzymatically produced oligonucleotides. (A) An atomic force microscopy scan of a two-dimensional origami structure. (B) A transmission electron micrograph of a 3-dimensional multilayer structure. (C) A transmission electron micrograph of a small scaffold-free three-dimensional nanostructure.
Figure 9B:
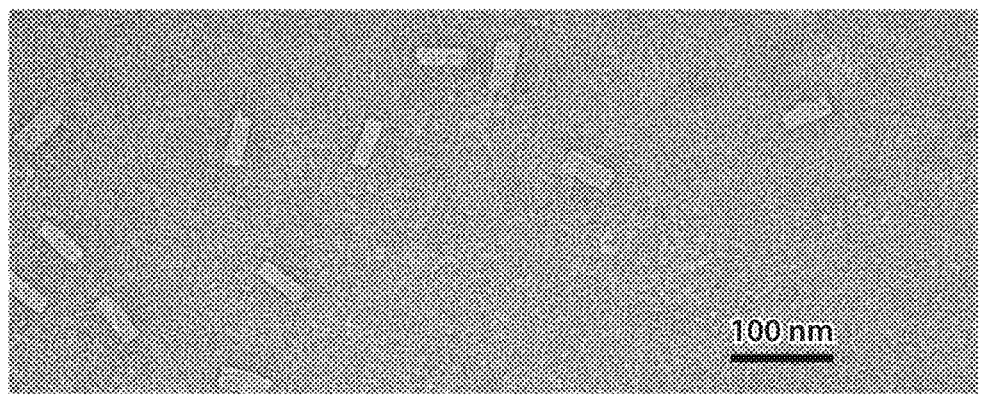
Figure 9C:
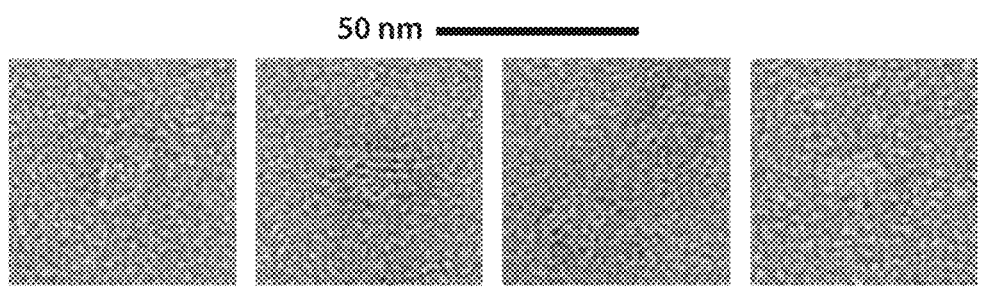

A "nicking primer" as used herein refers to a primer that is similar to the second round primer but contains the entire intron sequence. To facilitate the removal of the intron region and side products after a double nicking reaction, a nicking primer can be extended by ~10-30 nucleotides. In some embodiments, this extension can be captured by DNA affinity chromatography (FIG. 7). Preliminary data suggest that a 3' extension of the nicking primer (or nicking helper strand) with 2 degenerate nucleotides (NN) increases the efficiency of enzyme nicking.

In some embodiments, the nucleic acids amplified by the methods of the invention may be purified. Examples of nucleic acid purification methods that may be used in accordance with the invention include, without limitation, extraction, precipitation and differential solubilization, ultracentrifugation and chromatographic methods such as, for example, size exclusion chromatography, hydrophobic interaction chromatography, ion exchange chromatography, affinity chromatography, metal binding, immunoaffinity chromatography, silica columns such as PCR purification kits and high performance liquid chromatography (HPLC). In some embodiments, HPLC may be used to purify the nucleic acids (e.g., staple strands). Other nucleic acid purification methods may also be used.

Any one of the nucleic acids or methods provided herein can be used to assemble a two- or three-dimension DNA nanostructure (e.g., DNA origami structure). Methods for assembling such nanostructures are known in the art, any one of which may be used herein. Such methods are described by, for example, Bellot G. et al., *Nature Methods*, 8: 192-194 (2011); Liedl T. et al., *Nature Nanotechnology*, 5: 520-524 (2010); Shih W. M. et al., *Curr. Opin. Struct. Biol.*, 20: 276-282 (2010); Ke Y. et al., *J. Am. Chem. Soc.*, 131: 15903-08 (2009); Dietz H. et al., *Science*, 325: 725-30 (2009); Hogberg B. et al., *J. Am. Chem. Soc.*, 131: 9154-55 (2009); Douglas S. M. et al., *Nature*, 459: 414-418 (2009); Jungmann R. et al., *J. Am. Chem. Soc.*, 130: 10062-63 (2008); Shih W. M., *Nature Materials*, 7: 98-100 (2008); and Shih W. M., *Nature*, 427: 618-21 (2004), each of which is incorporated herein by reference in its entirety.

In some embodiments, the methods described herein may further comprise hybridizing a plurality of oligonucleotides with a scaffold strand to produce a DNA nanostructure. In some embodiments, a "scaffold strand" includes a long stretch of DNA containing sections of nucleotide sequences that are complementary to particular staple strands. In some embodiments, a scaffold strand is at least 100 nucleotides in length. In some embodiments, a scaffold strand is at least 500, at least 1000, at least 2000, at least 3000, at least 4000, at least 5000, at least 6000, at least 7000, or at least 8000 nucleotides in length. In some embodiments, a scaffold strand is less than 100 nucleotides in length.

In some embodiments, DNA nanostructures are produced in the absence of a scaffold strand (e.g., a scaffold-free structure).

In some embodiments, the invention provides methods of adjusting the stoichiometric ratio of target sequences in a composition. Generally, amplifying target sequences (e.g., staple strands) may result in a composition having different molar ratios of the staple strands. For applications that may require exact, or near exact, equimolar ratios of target sequence, the stoichiometry of the target sequence may be adjusted with the use of a long "helper scaffold" and a short "nicking helper strand," as depicted in FIG. 10C. A "helper scaffold," as used herein, refers to a single-stranded nucleic acid having multiple sequences, each sequence complementary to a unique binding sequence of an amplified target nucleic acid (a nucleic acid that contains a target sequence). Thus, in most instances, no two binding sequences of a helper scaffold are the same. In some embodiments, the sequences are arranged in a contiguous fashion along the nucleic acid helper scaffold. For example, a single composition may contain three populations of target nucleic acids, A, B and C, each of A, B and C containing a unique binding sequence and a unique target sequence. Equimolar ratios of A, B, and C target sequences may be obtained by using a helper scaffold having, for example, three sequences, one complementary to each of the unique binding sequences of A, B, and C, as shown in FIG. 10C. It is to be understood that the molar ratio of any number of sequences may be adjusted in this manner. For example, up to and including 5, 10, 15, 20, 30, 40, 50, 60, 70, 80, 90, 100, 120, 140, 160, 180, or 200 or more different sequences may be adjusted to achieve equimolar ratios using this approach.

In some embodiments, the target nucleic acids also have a common nicking sequence, which may be used to release the target sequence from the nucleic acid. A "nicking helper strand," as used herein, refers to a short sequence complementary to a common nicking sequence (e.g., a sequence common to each target nucleic acid). For example, each target nucleic A, B and C, described above, may contain a common nicking sequence, The nicking helper strand has a sequence complementary to the common nicking sequence and thus binds to the common nicking sequence of each target nucleic acid to form double-stranded regions. These double stranded regions form an enzyme cleavage site. Addition to the composition of an enzyme that recognizes the cleavage site will result in cleavage and release of the target sequences The recovered target sequences are typically present in equimolar amounts. This is illustrated in FIGS. 10A-10C.

In some embodiments, the helper scaffold may comprise at least two unique sequences. In some embodiments, the helper strand may comprise at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, at least 80, at least 90, at least 100, at least 120, at least 140, at least 160, at least 180, at least 200, at least 220, at least 240, at least 260, at least 280, at least 300, or more unique sequences. In some embodiments, the unique sequences have a length of about 5 to about 50 nucleotides, or they may be longer. For example, a unique sequence may have a length of about 5, about 10, about 20, about 30, about 40, or about 50 nucleotides. Thus, in some embodiments, a target nucleic acid may comprise a unique binding sequence having a length of about 5 to about 50 nucleotides, or more, or about 5, about 10, about 20, about 30, about 40 or about 50 nucleotides.

In some embodiments, the nicking helper strand comprises a common nicking sequence having a length of about 5 to about 50 nucleotides, or more. In some embodiments, the nicking helper strand comprises a common nicking sequence having a length of about 5, about 10, about 20, about 30, about 40, about 50, about 60, about 70, about 80, about 90, about 100, about 120, about 140, about 160, about 180, about 200, about 220, about 240, about 260, about 280, about 300, or more nucleotides. Thus, in some embodiments, a target nucleic acid may comprise a common nicking sequence having a length of about 5 to about 50 nucleotides, or more, or about 5, about 10, about 20, about 30, about 40, or about 50 nucleotides.

Also provided herein are kits comprising the single-stranded nucleic acid, the circular nucleic acid, or the plurality of nucleic acids of any one of the embodiments described herein. In some embodiments, the kits may further comprise ligase enzyme and/or kinase enzyme and/or ligase buffer and/or kinase buffer and/or dNTP and/or primer and/or polymerase and/or nicking helper strand and/or helper scaffold. In some embodiments, the kits comprise instructions for amplifying any one of the nucleic acids or plurality of nucleic acids. In some embodiments, the kits may also comprise instructions for assembling a two- or three-dimensional DNA nanostructure.

It is to be understood that the resultant oligonucleotides generated using the methods of the invention can be used as staple strands in DNA nanostructure synthesis, as described herein, as well as for other purposes. For example, the methods described herein may be used in the production of primers for targeted sequencing, or oligonucleotides for gene and genome synthesis, or in multiplexed automated genome engineering (MAGE), or the production of fluorescent in situ hybridization (FISH) probes, and the like. Accordingly, the invention provides methods for generating nucleic acids suitable for these various purposes and applications and also the pools of nucleic acids themselves whether defined inherently or by the synthesis process. In some instances, the synthesis methods are carried out using detectably labeled components (such as detectably labeled nucleotides) to generate detectably labeled end-product. In some instances, the end-product is detectably labeled post-synthesis. Suitable detectable labels include but are not limited to radioisotopes, chemiluminescent compounds, enzyme or enzyme substrates, and the like.

The barcoded circlet-to-circle amplification (c2ca) methods of the invention demonstrate provide various advantages over prior art amplification methods (such as PCR). These include scalability, direct production of single-stranded DNA oligonucleotides, and the ability to produce and purify single-stranded oligonucleotides of different lengths in parallel. With respect to scalability, to produce the same amount of oligonucleotides that can be produced in a 500 µl reaction (typically a few nmole, e.g. in one single well of a deep-well 96-well plate), an entire 96-well plate or more of PCR reaction products have to be combined. The isothermal rolling circle amplification method of the invention allows for scale-up to produce near arbitrary amounts of oligonucleotides. The ability to directly synthesis single-stranded oligonucleotides avoids having to separate double-stranded PCR products, for example, by denaturing PAGE gels that can be very laborious and is associated with significant loss of material. Finally, the ability to produce and purify (in parallel) single-stranded oligonucleotides of differing lengths is practically impossible by PAGE separation of double-stranded PCR products since too many bands would have to be excised and pooled.

EXAMPLES

Example 1—Amplification of Staple Strands for Assembling a 6×6 Helices, 64 Base Pair Structures with One Rolling Circle Amplification In this particular example, a 6×6×64 single-stranded tile (SST) structure was chosen as a test object: "6×6" refers to the number of helices in the structure, and "64" refers to the length of the helices in bases. A "single-stranded tile" is a scaffold-free nucleic acid structure based on the design principles from Yin, P. *Science*, 321:824-826 (2008).

The total number of 150 strands were divided into 2 subgroups (X-strands and Y-strands). The members of a subgroup do not have any significant complementary sequences to each other. When combined, the two subgroups formed the 3D-nanostructure. For this example, one subgroup (Y-strands) was chosen to be amplified enzymatically. The target sequences of the 75 Y-strands were extended with two versions of intron sequences (V5 and V6).

Only one rolling circle amplification (the third round) and the final double nicking digest (FIGS. 2D-E) were carried out. Intron regions were cut from the concatemers by double nicking. The crude reaction product of the V6 nicking reaction was purified by anion exchange chromatography (FIG. 3A). The fractions were collected and concentrated by ethanol precipitation. The concentration of oligonucleotides was determined on a UV photometer.

Equimolar amounts of fractions 2 and 4 were combined with synthetic X-strands in Tris/EDTA/MgCl$_2$ buffer and annealed from 60° C. to 4° C. for three days.

Figure 3B:
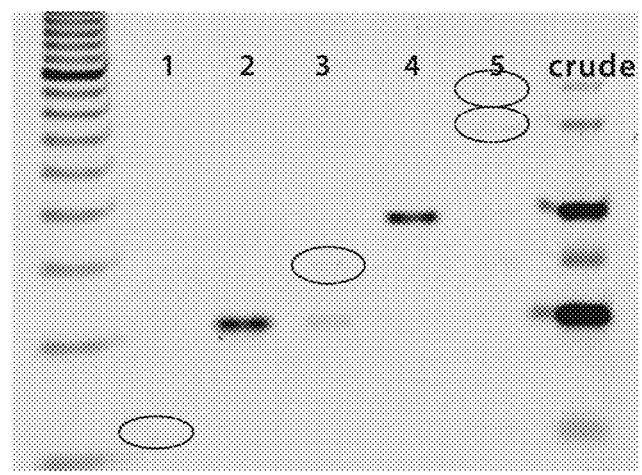
FIG. 3B shows a denaturing polyacrylamide gel electrophoresis (PAGE) image of the collected fractions and the crude product. Lane 1: nicking primers; lane 2: 32-mer target sequences; lane 3: excised common sequences (two nicking sites, the barcode sequence and the HindIII site); lane 4: 49-mer target sequences; lane 5: not completely nicked concatemers.
Figure 3C:
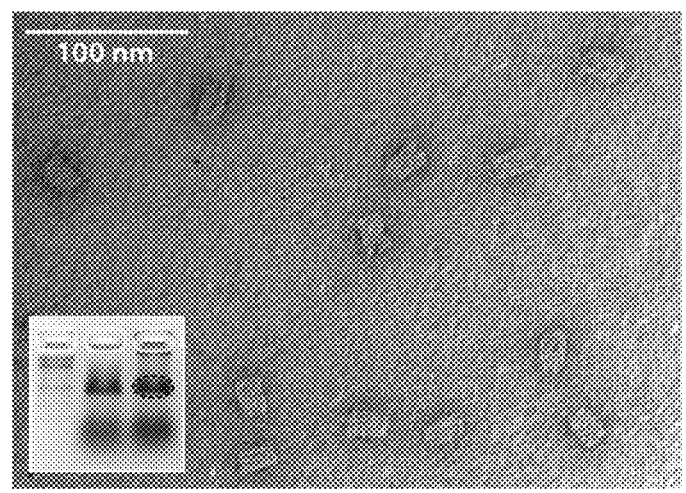
FIG. 3C shows a transmission electron micrograph of a test structure folded with the enzymatically produced oligonucleotides (i.e., target sequences 2 and 4). The inset shows a native agarose gel of two folding reactions: left with conventionally synthesized oligonucleotides, right with enzymatically produced oligonucleotides.

The folded structures were structures from excessive oligonucleotides on a native agarose gel (FIG. 3C inset). The band containing correctly folded product was excised and eluted by filtration centrifugation. The structures were imaged by transmission electron microscopy (FIG. 3C).

Amplification of the 75 Y-strands resulted in a yield of 37 µg, or 3 nmol, total (costing about $70 (USD)) (FIG. 3).

This example demonstrates that (a) a multiplexed circularization and rolling circle amplification can be carried out; (b) the resulting concatemers can be cut with nicking enzymes to produce only the staple strands; and (c) the staple strands can be incorporated with comparable or better yields to form a DNA nanostructure.

Example 2—Multiplexed Amplification

In this example, the staple strands for several DNA nanostructures (Table I) were amplified in parallel using the methods described (FIGS. 4A and B and FIG. 5), as follows.

Figure 4A:
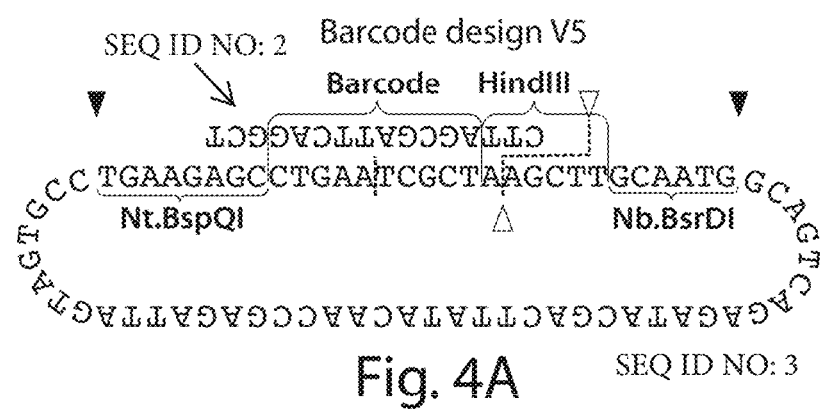
FIG. 4A is a schematic of a circular nucleic acid comprising a single subpool-specific barcode.
Figure 4B:
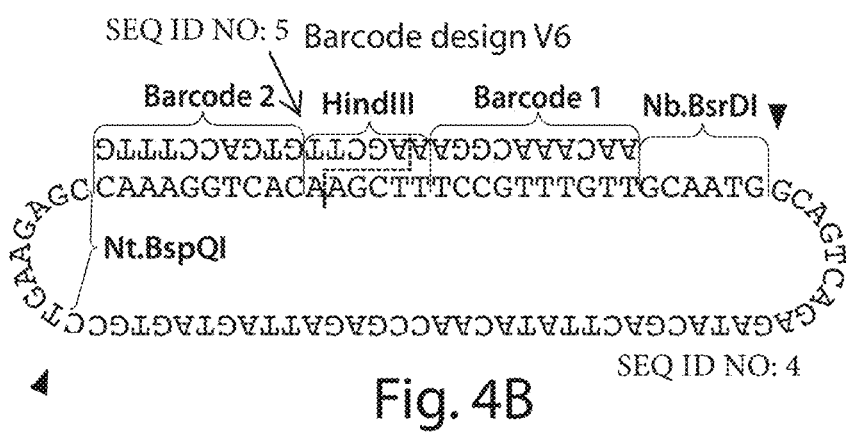
FIG. 4B is a schematic of a circular nucleic acid comprising two subpool-specific barcodes.

FIG. 4A is a schematic of a nucleic acid comprising a single barcode (the "V5" design) and FIG. 4B is a schematic of a nucleic acid comprising two barcodes (the "V6" design).

Figure 5:
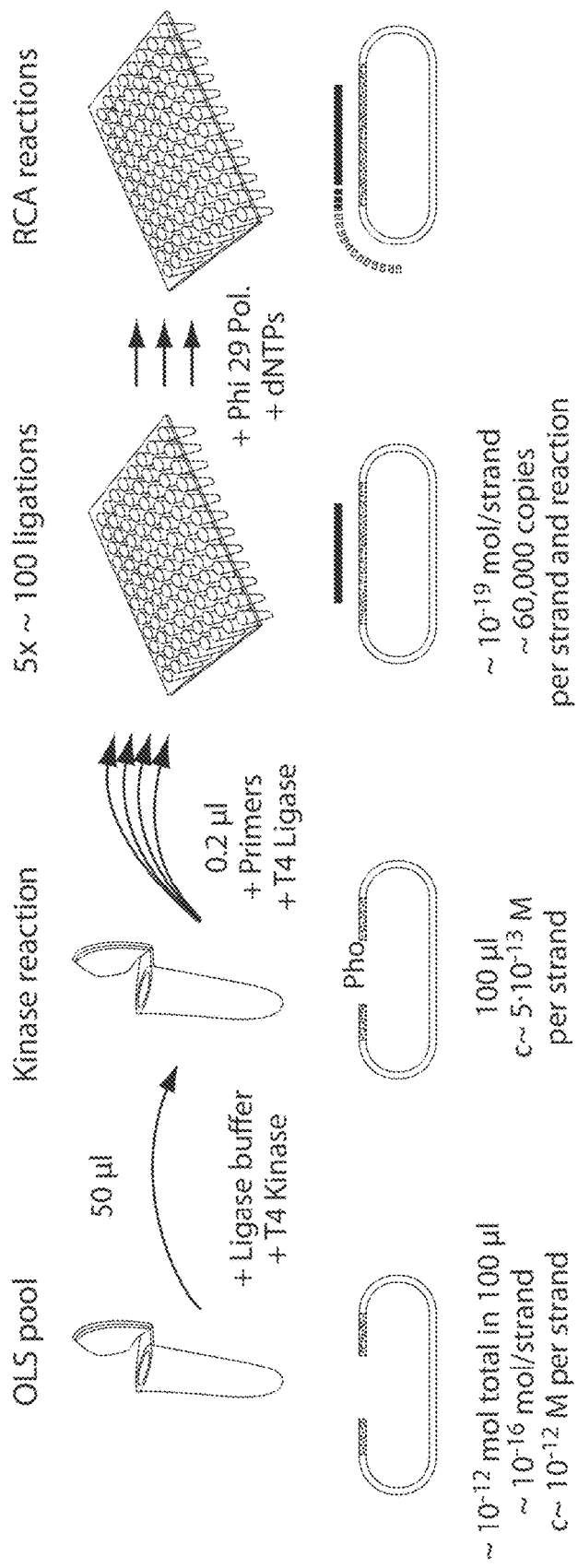
FIG. 5 is a schematic of another nucleic acid amplification method of the invention.

FIG. 5 is a schematic of the method used for the first round of circle-to-circle amplification in this particular example. T4 polynucleotide kinase (PNK), dNTPs (deoxyribonucleotide triphosphates), Nt.BspQI and NB.BsrDI were purchased from New England Biolabs. T4 Ligase (120 U/0) and Phi29 polymerase were purchased from Enzymatics.

First round of rolling circle amplification: Kinase reaction 150 µL of an AGILENT® OLS pool and 50 µl of a 1 pM solution mixture of the 75 Y-strands (INVITROGEN®) were incubated in a 100 µl reactions with 10 U of T4 PNK in Ligase buffer for 30 minutes at 37° C.

First circularization: 0.2 µl of the phosphorylated libraries were aliquoted into 16 different reaction tubes (150 µl PCR strips, AXYGEN®). One hundred fmol first round primer for the respective structure (see Table 1) were added and incubated at 65° C. for 2 minutes in 10 µl annealing buffer (5 mM Tris-HCl pH 7.6, 1 mM EDTA, 10 mM MgCl$_2$). The temperature was decreased at a rate of −0.1° C./sec to 25° C. Each reaction was supplemented with 24 U T4 ligase and ligation buffer (Enzymatics) and ligated at 25° C. for 20 min in 15 µl each. The enzyme was inactivated for 20 min at 65° C. and the temperature decreased at a rate of −0.1° C./sec to 25° C.

First rolling circle amplification: 2 U of Phi29 polymerase, BSA (bovine serum albumin) and dNTPs (to 1 mM each), and Phi 29 buffer were added to a total volume of 20 µl per reaction. The reaction was incubated for 1 h at 30° C. and heat inactivated.

Second round: 1 pmol of the respective second round primers were added to each reaction and annealed from 95° C. to 25° C. at −0.1° C./sec. Four units (U) of HindIII and NEBuffer2 (50 mM NaCl, 10 mM Tris-HCl, 10 mM MgCl$_2$, 1 mM Dithiothreitol=DTT; pH 7.9 @ 25° C.) were added to a total volume of 25 µl per reaction. The reaction was incubated for 1 hour at 37° C. and 20 min at 65° C. The temperature was decreased to 25° C. at −0.1° C./sec. The second round primer was then annealed to the monomers.

Re-ligation: ATP (to 1 mM), DTT (to 10 mM) and 48 U of T4 ligase and water were added to a final volume of 25 µl and incubated for 20 min at 25° C. and 10 min at 65° C. The temperature was decreased to 25° C. at −0.1° C./sec.

RCA 2: 60 U phi29 polymerase, 0.35 µl BSA solution and Phi29 buffer and dNTPs (to 1 mM) were added to 35 µl and were incubated for 8 h @ 30° C. and 20 min @ 65° C.

Third round: 100 pmol of the respective second round primers were added to each reaction and annealed from 95° C. to 25° C. at −0.1° C./sec.

Ten units of HindIII and NEBuffer2 were added to a total volume of 45 µl per reaction. The reaction was incubated for 1 h at 37° C. and 20 min at 65° C. The temperature was decreased to 25° C. at −0.1° C./sec.

Re-ligation: ATP (to 1 mM), DTT (to 10 mM) and 72 U of T4 ligase and water were added to a final volume of 55 µl and incubated for 20 min at 25° C. and 10 min at 65° C. The temperature was decreased to 25° C. at −0.1° C./sec.

Full scale third RCA reaction: 150 U (15 µl) phi29 polymerase, 5 µl BSA solution and Phi29 buffer were added to 500 µl and were incubated for 8 h @ 30° C. and 20 min @65° C. (for the gels shown in FIG. 6, only 1/10 of this reaction was carried out in 50 µl reactions).

Full scale double nicking reaction: 10 nmol of the respective second round primers were added to each reaction and annealed from 95° C. to 25° C. at −0.1° C./sec. 150 U of Nt.BspQI, 450 U of Nb.BsrDI and NEBuffer2 were added to a total volume of 1.5 ml. The reaction was incubated at 50° C. for 8 hours in an Eppendorf ThermoMixer. The reactions were vortexed for 5 seconds at 1000 rpm every 5 minutes (for the gel in FIG. 6, only 1/10 of the reaction was carried out in 150 µl).

Figure 6A:
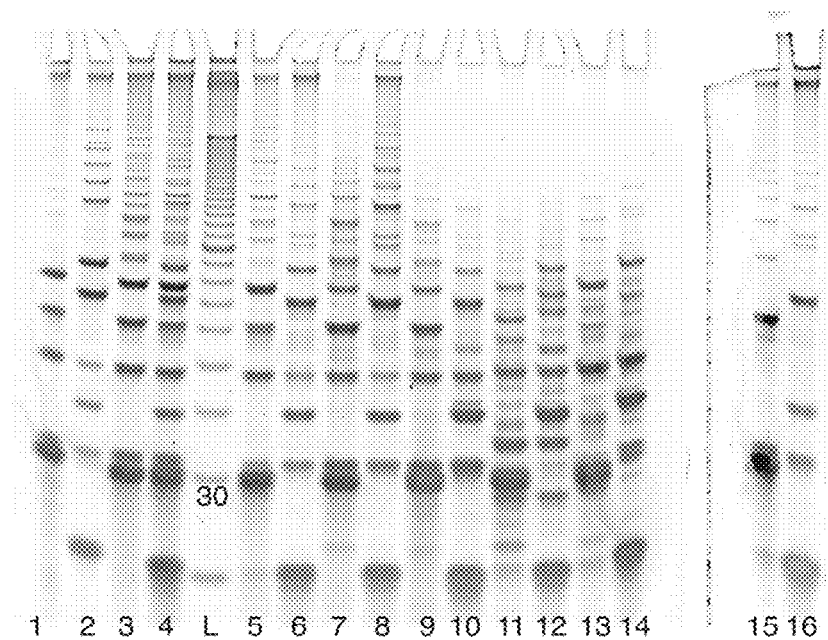
FIGS. 6A and 6B are photographs of polyacrylamide gels showing the distribution of reaction components (e.g., products) following the double nicking reaction after 3 rounds of rolling circle amplification. Lanes 1-2 are amplified from a mixture of 75 conventionally synthesized oligonucleotides (INVITROGEN®) and lanes 3-4 and 5-16 are amplified from a OLS pool (AGILENT®). Lane 1; 6×6×64 X (X-strands of a scaffold-free 6×6×64 single-stranded tile structure, amplified from diluted INVITROGEN® pool), barcode design V5; lane 2: 6×6×64 X, V6, INVITROGEN®; lane 3: 6×6×64 X V5 AGILENT®; lane 4: 6×6×64 X V6, L: 10 base pair (bp) ladder; lane 5: 6×6×64 Y, V5; lane 6: 6×6×64 Y, V6; lane 7: 10×10×160 X V5; lane 8: 10×10×160 X V6; lane 9: 10×10×160 Y V5; lane 10: 10×10×160 Y V6; lane 11: 24 helix bundle (hb) V5; lane 12: 24 hb V6; lane 13: 48 hb V5; lane 14: 48 hb V6; lane 15: 2D rectangle (same as Rothemund, Nature 2006) V5; lane 16: rectangle V6.
Figure 6B:
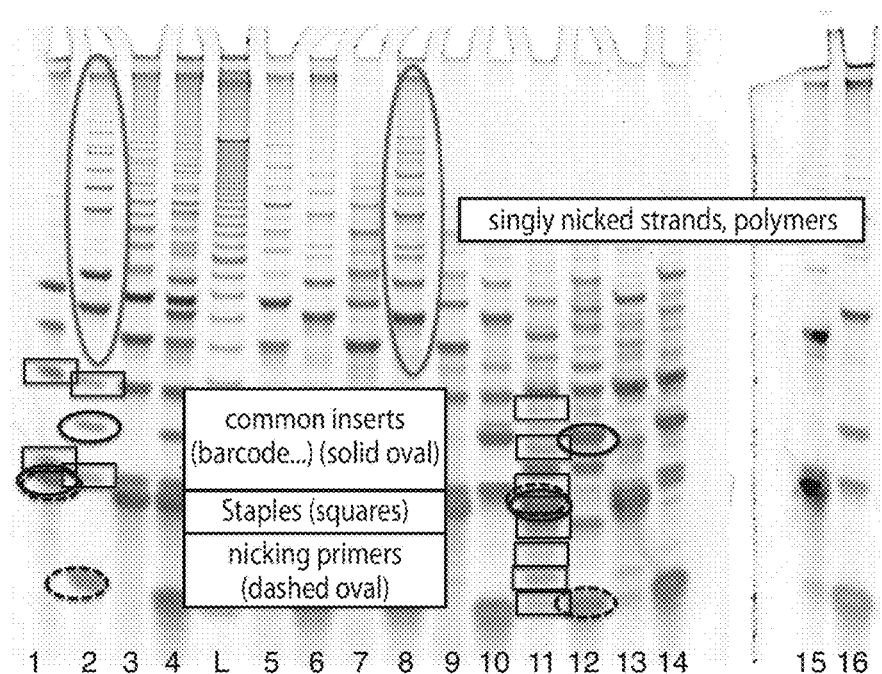

FIGS. 6A and B show an image of a polyacrylamide gel loaded with the product of each reaction (defined by the intended end-product nanostructure of Table I). For example, lane 1 of FIGS. 6A and B was loaded with the double nicking reaction product from a reaction designed to amplify staple strands for a 6×6×64 Y structure using a V5 barcode design.

Results show that the amplification reactions were robust, had high yields, and were subpool-specific, and there were no signs of non-specific background amplification.

TABLE I

| Structure, source of template | Barcode | Gel Lane |
|---|---|---|
| 6 × 6 × 64 X (Invitrogen) | V5 | 1 |
| 6 × 6 × 64 X (Invitrogen) | V6 | 2 |
| 6 × 6 × 64 X (Agilent OLS pool) | V5 | 3 |
| 6 × 6 × 64 X (rest all Agilent) | V6 | 4 |
| 6 × 6 × 64 Y | V5 | 5 |
| 6 × 6 × 64 Y | V6 | 6 |
| 10 × 10 × 160 X | V5 | 7 |

TABLE I-continued

| Structure, source of template | Barcode | Gel Lane |
|---|---|---|
| 10 × 10 × 160 X | V6 | 8 |
| 10 × 10 × 160 Y | V5 | 9 |
| 10 × 10 × 160 Y | V6 | 10 |
| 24 hb V8 | V5 | 11 |
| 24 hb V8 | V6 | 12 |
| 48 hb | V5 | 13 |
| 48 hb | V6 | 14 |
| Rothemund rectangle | V5 | 15 |
| Rothemund rectangle | V6 | 16 |

Each of the foregoing patents, patent applications, journal articles, and other references is hereby incorporated by reference in its entirety.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Multiple elements listed with "and/or" should be construed in the same fashion, e.g., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in some embodiment, to B only (optionally including elements other than A); in yet some embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in some embodiments, to at least one, optionally including more than one, B, with no A present (and optionally including elements other than A); in yet some embodiments, to at least one, optionally including more than one, A, and at least one, optionally including more than one, B (and optionally including other elements).

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition comprising:
   (a) a single-stranded template nucleic acid comprising
   a target sequence,
   a 5' end having a first sequence, and
   a 3' end having a second sequence such that, when the 5' end and the 3' end are juxtaposed, the first sequence and the second sequence form a subpool-specific region, wherein the subpool-specific region comprises a subpool-specific sequence and an endonuclease site and is flanked on each end by a nicking site; and
   (b) a primer that is complementary to and hybridizes to the subpool-specific sequence, wherein the target sequence is about 15 to about 100 nucleotides in length.

2. The composition of claim 1, wherein when the 5' end and the 3' end are juxtaposed, they are not covalently linked.

3. A composition comprising:
   (a) a single-stranded template nucleic acid comprising
   a target sequence,
   a 5' end having a first sequence, and
   a 3' end having a second sequence such that, when the 5' end and the 3' end are juxtaposed, the first sequence and the second sequence form a subpool-specific region, wherein the subpool-specific region comprises a subpool-specific sequence and an endonuclease site and is flanked on each end by a nicking site; and
   (b) a primer that is complementary to and hybridizes to the subpool-specific sequence, wherein the subpool-specific region comprises at least two subpool-specific sequences, each subpool-specific sequence comprising an endonuclease site.

4. The composition of claim 1, wherein the subpool-specific sequence is about 8 to about 20 nucleotides in length.

5. The composition of claim 1, wherein the endonuclease site is unique.

6. A composition comprising:
   (a) a single-stranded template nucleic acid comprising
   a target sequence,
   a 5' end having a first sequence, and
   a 3' end having a second sequence such that, when the 5' end and the 3' end are juxtaposed, the first sequence and the second sequence form a subpool-specific region, wherein the subpool-specific region comprises a subpool-specific sequence and an endonuclease site and is flanked on each end by a nicking site; and
   (b) a primer that is complementary to and hybridizes to the subpool-specific sequence, wherein the nicking sites are the same.

7. The composition of claim 1, wherein the primer is hybridized to the subpool-specific sequence.

8. A composition comprising
   (a) a plurality of single-stranded nucleic acids, each comprising a target sequence,
   a 5' end having a first sequence, and
   a 3' end having a second sequence such that, when the 5' end and the 3' end are juxtaposed, the first sequence and the second sequence form a subpool-specific region, wherein the subpool-specific region comprises a subpool-specific sequence and an endonuclease site and is flanked on each end by a nicking site; and
   (b) a plurality of primers that are complementary to and hybridize to the subpool-specific sequences, wherein the plurality of single-stranded nucleic acids comprises at least two subpools of single-stranded nucleic acids, each subpool having a unique subpool-specific sequence.

9. The composition of claim 8, wherein each subpool comprises 1 to 1000 different target sequences.

10. The composition of claim 9, wherein the target sequences are single-stranded DNA strands.

11. A method comprising:
    combining in a reaction mixture (a) a plurality of single-stranded nucleic acids, wherein each single-stranded nucleic acid comprises
    a target sequence,
    a 5' end having a first sequence, and
    a 3' end having a second sequence such that, when the 5' end and the 3' end are juxtaposed, the first sequence and the second sequence form a subpool-specific region, wherein the subpool-specific region comprises a subpool-specific sequence and an endonuclease site and is flanked on each end by a nicking site, (b) ligase, and (c) a first primer that is complementary to and hybridizes to the subpool-specific sequence;
    amplifying single-stranded nucleic acids using the first primer via rolling circle amplification to produce a first plurality of concatemers;

contacting the first plurality of concatemers with a second primer that is complementary to and hybridizes to a sequence complementary to the subpool-specific sequence and digesting the first plurality of concatemers with an endonuclease to produce a first plurality of monomers;

contacting the first plurality of monomers with ligase in the presence of the second primer;

amplifying the first plurality of monomers from the second primer via rolling circle amplification to produce a second plurality of concatemers.

12. The method of claim 11 further comprising:

contacting the second plurality of concatemers with a third primer that is complementary to and hybridizes to the subpool-specific sequence and digesting the second plurality of concatemers with an endonuclease to produce a second plurality of monomers;

contacting the second plurality of monomers with ligase in the presence of the third primer; and amplifying the second plurality of monomers from the third primer via rolling circle amplification to produce a third plurality of concatemers.

13. The method of claim 11, wherein when the 5' end and the 3' end are juxtaposed, they are not covalently linked.

14. The method of claim 11, wherein the subpool-specific sequence is about 8 to about 20 nucleotides in length.

15. The method of claim 11, wherein the endonuclease site is unique.

16. The method of claim 11, wherein the nicking sites are the same.

* * * * *